(12) United States Patent
Short

(10) Patent No.: US 6,838,238 B1
(45) Date of Patent: Jan. 4, 2005

(54) MORPHATIDES: NOVEL SHAPE AND STRUCTURE LIBRARIES

(75) Inventor: Jay M. Short, Encinitas, CA (US)

(73) Assignee: Invitrogen Corporation, Carlsbad, CA (US)

(*) Notice: Subject to any disclaimer, the term of this patent is extended or adjusted under 35 U.S.C. 154(b) by 0 days.

(21) Appl. No.: 08/839,468

(22) Filed: Apr. 14, 1997

Related U.S. Application Data

(60) Provisional application No. 60/028,527, filed on Oct. 17, 1996.

(51) Int. Cl.[7] ............................ C12Q 1/68; G01N 33/53
(52) U.S. Cl. .............................. 435/6; 435/7.1; 435/23; 435/91.1; 435/91.2; 435/183; 435/270; 536/24.2; 536/24.3; 536/23.1; 530/350; 544/69; 544/81
(58) Field of Search ................................ 435/6, 7.1, 23, 435/91.1, 91.2, 183, 270; 536/24.2, 24.3, 23.1, 22.1; 530/350; 544/69, 81; 935/77, 78

(56) References Cited

U.S. PATENT DOCUMENTS

| | | | |
|---|---|---|---|
| 4,959,309 A | | 9/1990 | Dattagupta et al. ............ 435/6 |
| 5,270,163 A | | 12/1993 | Gold et al. ..................... 435/6 |
| 5,270,170 A | * | 12/1993 | Schatz et al. ............... 435/7.37 |
| 5,434,257 A | * | 7/1995 | Matteucci et al. .......... 536/24.1 |
| 5,475,096 A | | 12/1995 | Gold et al. ..................... 536/26 |
| 5,510,240 A | * | 4/1996 | Lam et al. ..................... 435/7.1 |
| 5,660,985 A | | 8/1997 | Pieken et al. .................. 435/6 |
| 5,683,867 A | * | 11/1997 | Biesecker et al. ............. 435/6 |
| 5,705,337 A | | 1/1998 | Gold et al. ..................... 435/6 |
| 5,714,330 A | * | 2/1998 | Brenner et al. ................ 435/6 |
| 5,739,305 A | * | 4/1998 | Cubicciotti ................ 536/23.1 |
| 5,859,210 A | * | 1/1999 | Stowolitz et al. ........ 530/391.1 |

FOREIGN PATENT DOCUMENTS

| | | | |
|---|---|---|---|
| GB | 2 183 661 | 6/1987 | ............ C12N/15/00 |
| WO | WO 95/31429 | 11/1925 | ......... C07C/205/00 |
| WO | WO 89/06694 | 7/1989 | ............ C12P/21/00 |
| WO | WO 91/14696 | 10/1991 | ............ C07H/17/00 |
| WO | WO 92/14843 | 9/1992 | ............ C12Q/1/68 |
| WO | WO 95/07364 | 3/1995 | ............ C12Q/1/68 |
| WO | WO 95/08003 | 3/1995 | ............ C12Q/1/68 |
| WO | WO 95/20591 | 8/1995 | |
| WO | WO 95/22625 | 8/1995 | ............ C12Q/1/68 |
| WO | WO9604403 | 2/1996 | |
| WO | WO 96/08274 | 3/1996 | .......... A61K/47/48 |
| WO | WO9609316 | 3/1996 | |
| WO | WO9627605 | 9/1996 | |

OTHER PUBLICATIONS

J Rudinger Peptide Hormones (JA Parsons Ed. Jun. 1976) pp. 1–6.*
Maxam, A.M. and Gilbert, W. "A New Method for Sequencing DNA" Proc. Natl. Acad. Sci. USA 74: 560–564 (1977).
Ren, X.F. et al. "Formation of Stable DNA Loops by Incorporation of Nonpolar, Non–Hydrogen–Bonding Nucleoside Isosteres" Angew. Chem. Int. Ed. Engl. 35: 743–746 (1996).
McCorkle, G.M. and Altman, S. "RNA's as Catalysts" Journal of Chemical Education 64: 221–226 (1987).
Sakthivel, et al. "Expanding the Potential of DNA for Binding and Catalysis: Highly Functionalized dUTP Derivatives That are Substrates for Thermostable DNA Polymerases", Angew.Chem. Int. Ed. vol. 37(20) 2872–2875 (1998).
Smith, et al. "In Vitro Selection Without Intervening Amplification", Angew. Chem. Int. Ed. vol. 36(17) 1879–1881 (1997).
Bartel, D.P. and Szostak, J.W. "Isolation of New Ribozymes from a Large Pool of Random Sequences" Science 261: 1411–1418 (1993).
Beaudry, A.A. and Joyce, G.F. "Directed Evolution of an RNA Enzyme" Science 257: 635–641 (1992).
Cech, T.R. "The Chemistry of Self–Splicing RNA and RNA Enzymes" Science 236: 1532–1539 (1987).

(List continued on next page.)

Primary Examiner—Bennett Celsa
(74) Attorney, Agent, or Firm—Gray Cary Ware & Freidenrich, LLP

(57) ABSTRACT

This invention provides a method for identifying one or more complexes from a library of complexes, wherein said complex or complexes are selected for their ability to perform a preselected or desired function on a target molecule or by having a pre-selected structure, each complex being designated a morphatide, said method comprising: (a) preparing a library of morphatides, comprised of: (i) a scaffolding component selected from the group consisting of nucleic acid, nucleic acid like molecule or nucleic acid analog having one or more regions of randomized sequence; (ii) one or more linker components; and (iii) one or more agent molecules or type of agent molecules, linked to the scaffolding component by one or more type of linker components; and (b)screening the library of morphatides prepared in step (a) by contacting, binding, or associating the morphatides with one or more suitable target molecules upon which a morphatide performs a preselected or desired function or to which a morphatide binds or associates through a pre-selected structure of said morphatide under conditions permitting said morphatide to perform said preselected or desired function on said target molecules or permitting said morphatide to bind or associate with said target molecules through the preselected structure; (c) separating the morphatides performing the preselected or desired function or binding or associating through the preselected structure, from the library of morphatides and target molecules; thereby identifying one or more complexes from a library of complexes, wherein said complex or complexes are selected for their ability to perform a preselected or desired function on a target molecule or by having a pre-selected structure.

23 Claims, 7 Drawing Sheets

OTHER PUBLICATIONS

Crouch, G.J. and Eaton, B.E. "Synthesis of 2'–Deoxyuridine Nucleosides with Appended 5–Position Carbonyl Cross–Linking Groups" Nucleosides & Nucleotides 13: 939–944 (1994).

Lorsch, J.R. and Szostak, J.W. "In vitro Evolution of New Ribozymes with Polynucleotide Kinase Activity" Nature 371: 31–36 (1994).

McCorkle, G.M. and Altman, S. "RNA's as Catalysts" Concepts in Biochemistry 64: 221–(1987).

Pan, T. and Uhlenbeck, O.C. In Vitro Selection of RNAs That Undergo Autolytic Cleavage with $Pb^{2+}$ Biochemistry 31: 3887–3895 (1992).

Piccirilli, J.A. et al. "Aminoacyl Esterase Activity of the *Tetrahymena Ribozyme*" Science 256: 1420–1424 (1992).

Prudent, J.R. et al. "Expanding the Scope of RNA Catalysis" Science 264: 1924–1927 (1994).

Joyce, G.F. "Amplification, Mutation and Selection of Catalytic RNA" Gene 82: 83–87 (1989).

Joyce, G.F. and Inoue, T. "A Novel Technique for the Rapid Preparation of Mutant RNAs" Nucleic Acids Research 17: 711–714 (1989).

Ellington, A.D. and Szostak, J.W. Abstract of papers presented at the 1990 meeting on RNA Processing. Cold Spring Harbor Laboratory, Cold Spring Harbor, NY, p. 226 (1990).

Kinzler, K.W. and Vogelstein, B. "Whole Genome PCR: Application to the Identification of Sequences Bound by Gene Regulatory Proteins" Nucleic Acids Research 17: 3645–3653 (1989).

Kramer, F.R. et al. "Evolution in vitro: Sequence and Phenotype of a Mutant RNA Resistant to Ethidium Bromide" J. Mol. Biol. 89: 719–736 (1974).

Levisohn, R. and Spiegelman, S. "Further Extracellular Darwinian Experiments with Replicating RNA Molecules: Diverse Variants Isolated Under Different Selective Conditions" Proc. Natl. Acad. Sci. USA 63: 805–811 (1969).

Levisohn, R. and Spiegelman, S. "The Cloning of a Self–Replicating RNA Molecule" Proc. Natl. Acad. Sci. USA 60: 866–872 (1968).

Oliphant, A.R. et al. "Defining the Sequence Specificity of DNA–Binding Proteins by Selecting Binding Sites from Random–Sequence Oligonucleotides Analysis of Yeast GCN4 Protein" Mol. Cell. Biol. 9: 2944–2949 (1989).

Oliphant, A.R. and Struhl, K. "Defining the Consensus Sequences of *E. coli* Promoter Elements by Random Selection" Nucleic Acids Research 16: 7673–7683 (1988).

Oliphant, A.R. and Struhl, L. "The Use of Random–Sequence Oligonucleotides for Determining Consensus Sequences" Methods in Enzymology 155: 568–582 (1987).

Oliphant, A.R. et al. "Cloning of Random–Sequence Oligodeoxynucleotides" Gene 44: 177–183 (1986).

Robertson, D.L. and Joyce, G.F. "Selection in vitro of an RNA Enzyme That Specifically Cleaves Single–Stranded DNA" Nature 344: 467–468 (1990).

Thiesen, H. and Bach, C. "Target Detection Assay (TDA): a Versatile Procedure to Determine DNA Binding Sites as Demonstrated on SP1 Protein" Nucleic Acids Research 18: 3203–3209 (1990).

Oleksyszyn, J. and Powers, J.C. "Irreversible Inhibition of Serine Proteases by Peptide Derivatives of (α–Aminoalkyl)phosphonate Diphenyl Esters" Biochemistry 30: 485–493 (1991).

Oleksyszyn, J. and Powers, J.C. "Irreversible Inhibition of Serine Proteases by Peptidyl Derivatives of α–Aminoalkylphosphonate Diphenyl Esters" Biochemical and Biophysical Research Communications 161: 143–149 (1989).

Simon, S. et al. "Inhibition of Human Neutrophil Elastase by Polyguanylic Acid and Other Synthetic Polynucleotides" Adv. Exp. Med. Biol. 240: 65–74 (1988).

Simon, S. et al. "Inhibition of Human Neutrophil Elastase by Polyguanylic Acid and Other Synthetic RNA Homopolymers" Exp. Lung Res. 14: 85–99 (1988).

Vered, M. et al. "Inhibition of Human Neutrophil Elastase by Bacterial Polyanions" Exp. Lung Res. 14: 67–83 (1988).

Abelson, J. "Directed Evolution of Nucleic Acids by Independent Replication and Selection" Science 249: 488–489 (1990).

Conrad, R. et al. "Isozyme–Specific Inhibition of Protein Kinase C by RNA Aptamers" J. Biol. Chem. 269:32051–32054 (1994).

Dewey, T.M. et al. "New Uridine Derivatives for Systematic Evolution of RNA Ligands by Exponential Enrichment" J. Am. Chem. Soc. 117: 8474–8475 (1995).

Freier, S.M. et al. "Mutational SURF': A Strategy for Improving Lead Compounds Identified from Combinatorial Libraries" Bioorganic & Medicinal Chemistry 4: 717–725 (1996).

Jensen, K.B. et al. "Characterization of an in Vitro–selected RNA Ligand to the HIV–1 Rev Protein" J. Mol. Biol. 235: 237–247 (1994).

Latham, J.A. et al. "The Application of a Modified Nucleotide in Aptamer Selection: Novel Thrombin Aptamers Containing 5–(1–Pentynyl)–2'–Deoxyuridine" Nucleic Acids Research 22: 2817–2822 (1994).

Lestienne, P. and Bieth, J.G. "Inhibition of Human Leucocyte Elastase by Polynucleotides" Biochimi 65: 49–52 (1983).

Ma, M.Y. et al. "Design and Synthesis of RNA Miniduplexes via a Synthetic Linker Approach" Biochemistry 32: 1751–1758 (1993).

Nelson, J. et al. "Incorporation of a Non–Nucleotide Bridge into Hairpin Oligonucleotides Capable of High–Affinity Binding to the Rev Protein of HIV–1" Biochemistry 35: 5339–5344 (1996).

Soukup, G. et al. "Preparation of Oligonucleotide–Biotin Conjugates with Cleavable Linkers" Bioconjugate Chem. 6: 135–138 (1995).

Tuerk, C. and Gold, L. "Systematic Evolution of Ligands by Exponential Enrichment: RNA Ligands to Bacteriophage T4 DNA Polymerase" Science 249: 505–510 (1990).

Tyagi, S. "Taking DNA Probes into a Protein World" Nature Biotechnology 14: 947–948 (1996).

Vlasova, I.E. and Vlasov, V.V. "Molecular Evolution: Design of Nucleic Acids Possessing Catalytic Properties and Capable of Specific Complex Formation" Molecular Biology 27: 1–5 (1993).

Wiegand, T. et al. "Selection of RNA Amide Synthases" Chemistry & Biology 4: 675–683 (1997).

Xu, W. and Ellington, A. "Anti–Peptide Aptamers Recognize Amino Acid Sequence and Bind a Protein Epitope" Proc. Natl. Acad. Sci. USA 93: 7475–7480 (1996).

* cited by examiner

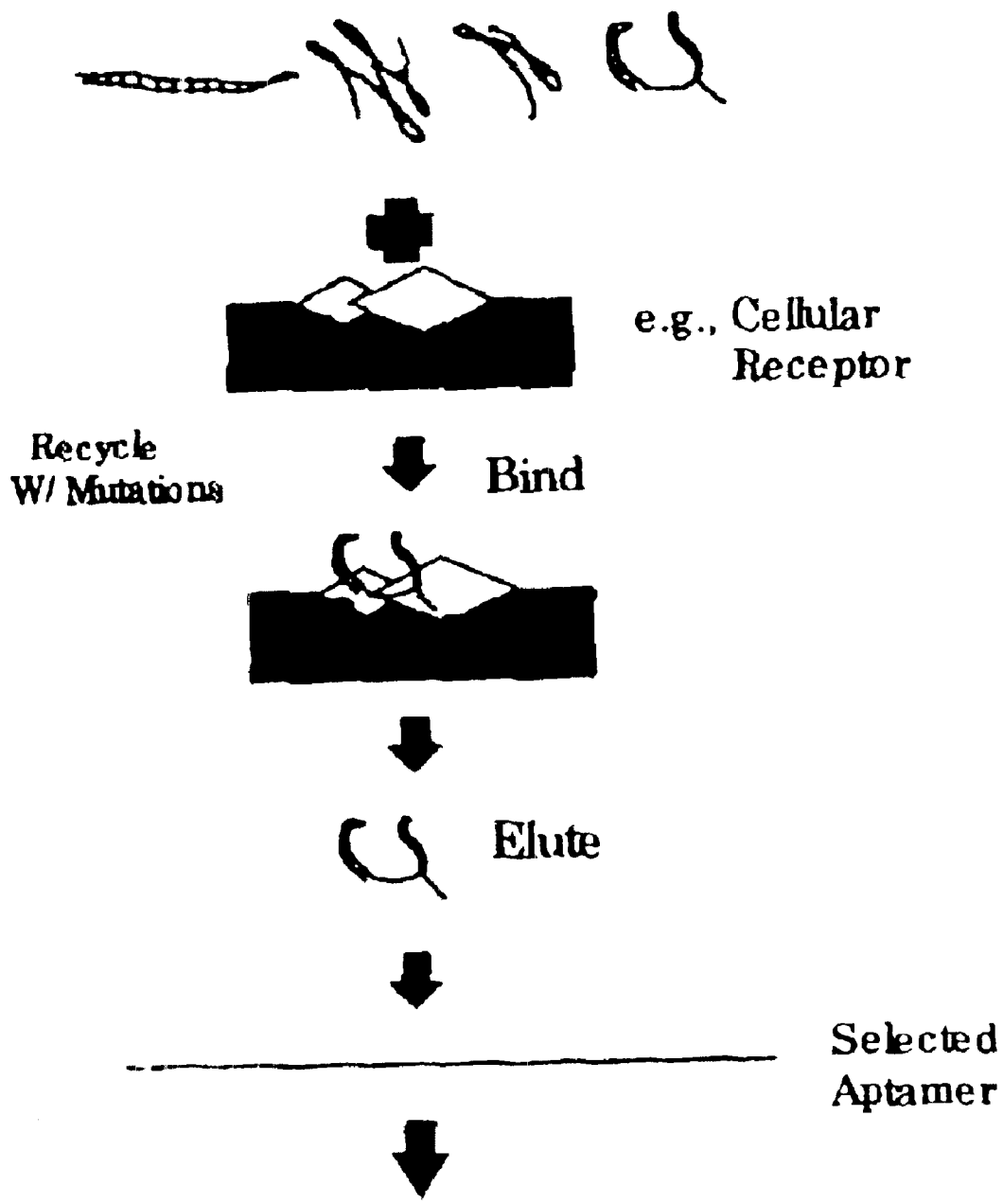

Aptamer Generation

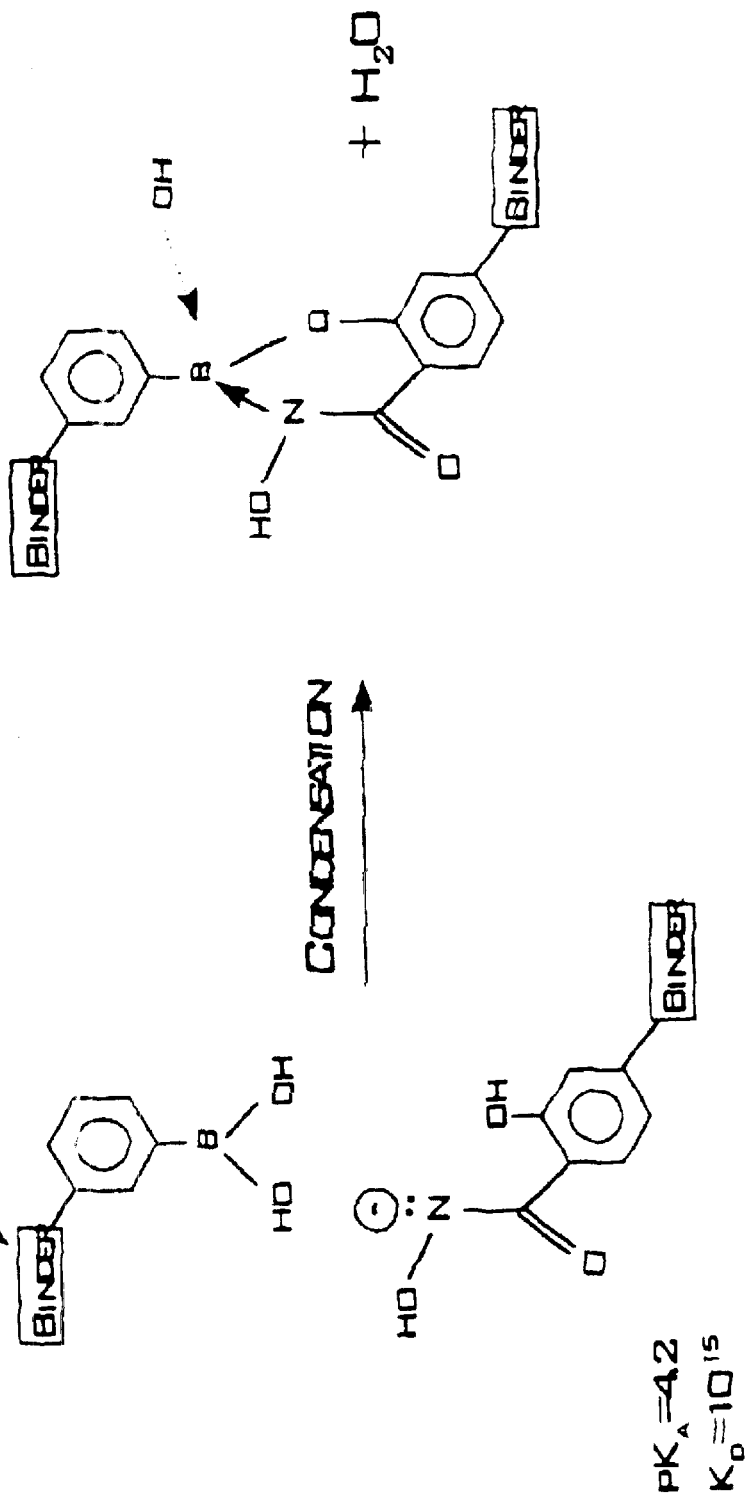

US 6,838,238 B1

MORPHATIDES: NOVEL SHAPE AND STRUCTURE LIBRARIES

This application claims the benefit of copending U.S. Provisional Application Ser. No. 60/028,527 filed Oct. 17, 1996.

Throughout this application, various references are referred to within parentheses. Disclosures of these publications in their entireties are hereby incorporated by reference into this application to more fully describe the state of the art to which this invention pertains. Full bibliographic citation for these references may be found at the end of this application, preceding the claims.

BACKGROUND OF THE INVENTION

The present invention relates to the production and screening of libraries of compounds and, more particularly, to the generation and screening of shape and structure libraries produced from large or small size molecules for the purpose of identifying potentially useful agents.

New agents for effectively modulating a range of biological processes have a variety of applications in industry, medicine and agriculture. The identification of structurally unique lead compounds is an important step in selecting such biologically useful agents. Historically and currently, mass screening of collections of large numbers of molecules (chemicals or other compounds) and mixtures of molecules, has been the most successful approach for identifying lead compounds. Most of these collections are either compound databases generated by pharmaceutical research, natural products collections, such as fermentation broths, or more recently, collections of peptides, nucleotides or other synthesized molecules.

Each of these collections, or "libraries", has its advantages as well as its limitations. Collections generated via research, such as compound databases, can obtain a potentially limitless repertoire of compounds for search (large numbers), however they tend to contain a limited number of diverse structures, representing only a small portion of the total structural diversity possibilities. Natural product libraries can offer structural complexity, however the difficulty in downstream manufacturing of these products, and of reducing leads to useful products is a serious limitation of this type of approach. Peptide libraries are limited to peptides or peptide mimics. There has been limited success in the conversion of peptide chemical leads into pharmaceutically useful drug candidates. These lead compounds are at a disadvantage for generating orally active drug candidates due to the complexity of determining their three dimensional structures for synthesis of small organic molecules and due to the sensitivity of their peptide bonds to acid hydrolysis. However, the structural diversity offered by this technology is its greatest advantage. Nucleotide libraries are also restricted to the genetic repertoire (nucleotides) or nucleotide analogues that preserve specific Watson-Crick pairing and can be copied by a polymerase, hence they are more limited in their useful structural diversity than peptide libraries, however this remains an advantage of these libraries. Nucleotide libraries also offer the capacity for cloning and amplification of DNA sequences, which allows for enrichment by serial selection and provides a facile method for decoding the structure of active molecules.

Compound databases have historically been generated via the chemical modification of existing compounds to generate analogs, which then follow the conventional paradigm of small molecule lead development in which a compound undergoes many rounds of individualized, hand-crafted modification and biological testing en route to drug candidacy. Natural product libraries are derived from collections of natural materials, such as fermentation broths, plant extracts, etc.

Peptide and nucleotide libraries are generated by sequence randomization of individual monomers using a single naturally existing biological linkage (3'-5' phosphate linkage of nucleotides or amide linkage of peptides). As indicated, the biggest advantage in using peptide and nucleotide libraries is the apparent structural diversity afforded with the technologies. For example, FIG. 1 briefly demonstrates one well known strategy for generating and utilizing "Aptamers", a library of nucleotide shapes.

For the discovery of drugs and other commercially valuable compounds, small molecule, highly complex libraries containing diverse functionalities have the greatest utility and provide the greatest chance of success. Libraries must also permit identification and evaluation of the structure/activity relationship of the potentially small fraction of active molecules among the larger number of inactive or less active compounds. To satisfy these needs, recent trends are to generate "chemical libraries" and new techniques to evaluate and screen them. "Chemical libraries" have been defined as "intentionally created collection of differing molecules which can be prepared synthetically or biosynthetically". A type of synthetic strategy which can lead to large chemical libraries is "combinatorial chemistry". "Combinatorial chemistry" has been defined as "the systematic and repetitive, covalent connection of a set of different 'building blocks' of varying structures to each other to yield a large array of diverse molecular entities." (Gallop, M. A. et al., 1994) Building blocks can include nucleotides, carbohydrates, peptides or peptoids into ordered structures. Chemical libraries generated utilizing combinatorial chemistry can display remarkable diversity. These large libraries can be selected for potential pharmacological activity by their affinity to specified ligands. Several groups have taken advantage of these facts to develop systems utilizing modified and unmodified oligonucleotides and modified and unmodified polypeptides as ligands to bind targets. Many examples are available in the art, a few of which are described herein.

Although oligonucleotides inherently have fewer potential building blocks to provide diversity, they have demonstrated a remarkable affinity for selected targets. Examples include both single-stranded RNA and single- and double-stranded DNA. A great attraction of nucleic acid based combinatorial chemistry is the potential for directed evolution. Repeated cycles of selection for the highest affinity and error-prone PCR can lead to increased diversity and oligomers with an even greater affinity.

The versatility of the binding capabilities of DNA and RNA oligonucleotides seems inexhaustible and the growing number of applications are a tribute to its enormous potential. One of the earliest polynucleotides of this type was directed to the human blood clotting enzyme thrombin (Bock et al., 1992). This study initiated a search for other thrombin inhibitors based on this approach (Bracht and Schroer, 1994; Kubik et al., 1994; Griffin et al., 1993). Numerous other polynucleotide sequences have been selected from initially random libraries of molecules. Examples include DNA and RNA oligomers selected against HIV integrase (Allen et al., 1995), its Rev protein (Giver et al., 1993; Tuerk and MacDougal-Waugh, 1993; Jensen et al., 1994; Jensen et al., 1995; Bartel et al., 1991), and its reverse transcriptase (Chen and Gold, 1994; Tuerk et al., 1992;

Schneider et al., 1995), as well as against reverse transcriptase of feline immunodeficiency virus (Chen et al., 1996). Other were developed against human growth factors, such as nerves GF (Binkley et al., 1995), vascular endothelial GF (Jellinek et al., 1994), and basic fibroblast GF (Jellinek et al., 1996; Jellinek et al., 1995) and against Qβ replicase (Brown and Gold, 1995a; Brown and Gold, 1995b). An RNA oligomer has been made against nucleolin (Ghisolfi-Nieto et al., 1996), an essential protein in ribosome biosynthesis. Oligomers against selectins may show potential in treatment of anti-inflammatory diseases (O'Connell et al., 1996). Other proteins against which these oligomers have been selected include immunoglobulin IgE (Wiegand et al., 1996), bacteriophage T4 DNA polymerase (Tuerk and Gold, 1990), bacteriophage R17 coat protein (Schneider et al., 1992), the E. coli rho factor (Schneider et al., 1993), leucine receptive regulatory protein (Cui et al., 1995) and several ribosomal proteins (Dobbelstein and Shenk, 1995; Ringquist et al., 1995).

These polynucleotides can also be selected for their affinity to small molecules. These include early experiments which demonstrated RNA oligomers that bind specifically to a variety of dye molecules (Ellington and Szostak, 1990). Later this finding was extended to DNA oligomers (Ellington and Szostak, 1992). Interestingly, the sequences of these DNA and RNA species are quite distinct, even when selected for the identical substrates.

The oligopeptide substance P, a mammalian neurotransmitter, was used to select RNA molecules with high affinity against the neurotransmitter by Nieuwlandt et al. (1995). Single amino acids and other small molecules are also able to bind such molecules. Examples include valine (Majerfeld and Yarus, 1994), arginine (Yarus and Majerfeld, 1992; Puglisis et al., 1992; Nolte et al., 1996; Hicke et al., 1989; Geiger et al., 1996; Burgstaller et al., 1995), citrulline (Burgstaller et al., 1995), ATP (Huizinga and Szostak, 1995; Sassanfar and Szostak, 1993), adenosine (Huizinga and Szostak, 1995), D-adenosine (Kluszmann et al., 1996), flavin mono-nucleotide (Fan et al., 1996), theophylline (Jenison et al., 1994), cyanocobalamine (Lorsch and Szostak, 1994).

Another interesting potential of these oligomers was pursued by Morris et al. (1994) who tried unsuccessfully to select for a molecule specific for a reaction transition state, effectively attempting to create a catalyst, Hale and Schimmel (1996), however, did succeed in generating a DNA molecule that induces hydrolysis of a misactivated amino acid bound to a tRNA synthetase, a case of protein synthesis editing. Lorsch and Szostak (1994) succeeded in selecting for several RNA aptamers with 2' or 5' polynucleotide kinase activity.

Polynucleotides with modifications of incorporated nucleotides have been selected by Latham et al. (1994), who incorporated 5-(1-pentynyl)-2'-deoxyuridine into thrombin binding DNA molecules. The primary sequence of these modified DNA oligomers was strikingly different from the unmodified DNA molecule.

The use of nucleic acids for therapeutic and diagnostic applications often requires their stability in biological fluids. Aside from chemical modification, nuclease-resistant ligands can be generated by using L-ribose-based nucleotides (Nolte et al. 1996, Klussmann et al. 1996). In this approach the conventional D-RNA directed against the optical mirror image of the target is selected first using repeated rounds of mutation and selection of the nucleic acid and subsequently the corresponding L-RNA is chemically synthesized. L-RNA's with specificity for L-arginine (38-mer, Kd=60 mM, Nolte et al 1996) and D-adenosine (58-mer, Kd=1.7 mM, Klussmann et al. 1996) have been isolated and shown to be stable in human serum at 37° C. Another example includes chirally pure methylphosphonate linkages that are suitable for generating oligomers capable of efficiently hybridizing with DNA or RNA and are highly resistant to metabolic breakdown in biological systems (Reynolds et al. 1996).

Another interesting method for the selection of nucleic acid molecules with highly specific binding to target molecules has been developed and termed "SELEX" (Systematic Evolutions of Ligands by EXponential enrichment), which is described in U.S. Pat. No. 5,270,163 entitled "Nucleic Acid Ligands" and in PCT/US91/04078. SELEX is a method for making a nucleic acid to a desired target molecule involving the selection from a mixture of candidate oligonucleotides and the step-wise iteration of binding, partitioning and amplifying, using the same general selection scheme, to achieve a desired criterion of binding affinity and selectivity. The basic SELEX method has also been modified to achieve a number of specific objectives. (For instance, those described in PCT/US94/10562 filed Sep. 19, 1994, and WO 96/09316 filed Sep. 19, 1995).

For example, SELEX has been used in conjunction with gel electrophoresis to select nucleic acid molecules with specific structural characteristics, such as bent DNA; as a method for selecting nucleic acid ligands containing photoreactive groups capable of binding and/or photo-crosslinking to and/or photoinactivating a target molecule; in the identification of certain nucleic acid sequences that contain 5-iodouracil residues and that covalently bind to HIV-I Rev protein; in the identification of highly specific nucleic acid ligands able to discriminate between the closely related molecules, theophylline and caffeine; as a method to achieve efficient partitioning between oligonucleotides having high and low affinity for a target molecule; and as a method for covalently linking a nucleic acid to its target.

The SELEX method relies on a process of selection and amplification for enrichment of desired candidate positives from a collection of candidates to identify better candidates or the best candidates from the collection. During the selection part of the process from each parent collection, the bulk binding of the populations of candidates becomes increasingly higher as the sequences are amplified, and those sequences unable to interact with the target are eliminated from the population. Hence, "evolution" of the population occurs due to the increased presence due to amplification of candidates which exhibit the desired activity and the effective elimination of undesirable candidates. Amplification is used to increase the presence of desirable products and to separate those products from those that do not react or have a weaker reaction with a target of interest. (WO 96/09316 entitled "Parallel Selex").

The Parallel SELEX method describes one potential technique for the identification of DNAs that have facilitating activities as measured by their ability to facilitate formation of a covalent bond between the DNA, including an associated functional unit, and its target. Although this method focuses on the facilitative binding capabilities of DNA, it does not take advantage of the potential for nucleic acids to be evolved in vitro via methods such as "Error-prone PCR" or "Sexual PCR". The method defines the pool, or collection, of DNAs as being "evolved" due to the enrichment of positives that occurs via an amplification reaction ("exponential enrichment"). The DNA molecules themselves are never evolved.

SUMMARY OF THE INVENTION

There currently exists need for novel systems which combine the advantages of screening the different types of collections mentioned; one which allows the enrichment by serial selection and facilitates the decoding of the structure of lead candidates afforded by screening nucleotides, and which simultaneously provides the potentially limitless repertoires of diverse molecules for screening offered by chemical compound and natural product collections. The present invention provides a novel approach for creating diverse, complex shape and structure libraries of large or small size agent molecules and for screening said libraries to identify compounds having a wide variety of commercially valuable industrial applications. Not only does the present invention provide a limitless repertoire of diverse structures that may be screened for biological activity, but it provides an iterative selection and enhancement process to define the most active compounds, and it is a process that allows one to solve the structure (if desired) of the most active compounds rapidly. These processes for mutating and selecting compounds to effectively "evolve" chemical groups in order to identify a most useful compound(s) and the ability to rapidly solve the structure of identified compounds are significant advantages of the present invention. These advantages and other features distinguish the present invention from previously existing technologies.

The present invention provides a method for identifying one or more complexes from a library of complexes, wherein said complex or complexes are selected for their ability to perform a preselected or desired function on a target molecule or by having a pre-selected structure, each complex being designated a morphatide said method comprising: (a) preparing a library of morphatides, comprised of: (i) a scaffolding component selected from the group consisting of nucleic acid, nucleic acid like molecule or nucleic acid analog having one or more regions of randomized sequence; (ii) one or more linker components; and (iii) one or more agent molecules or type of agent molecules, linked to the scaffolding component by one or more type of linker components; and (b) screening the library of morphatides prepared in step (a) by contacting, binding, or associating the morphatides with one or more suitable target molecules upon which a morphatide performs a preselected or desired function or to which a morphatide binds or associates through a pre-selected structure of said morphatide under conditions permitting said morphatide to perform said preselected or desired function on said target molecules or permitting said morphatide to bind or associate with said target molecules through the preselected structure; (c) separating the morphatides performing the preselected or desired function or binding or associating through the preselected structure, from the library of morphatides and target molecules; thereby identifying one or more complexes from a library of complexes, wherein said complex or complexes are selected for their ability to perform a preselected or desired function on a target molecule or by having a pre-selected structure.

The present invention also provides a method for identifying one or more complexes from a library of complexes, wherein said complex or complexes are selected for their ability to perform a preselected or desired function on a target molecule or by having a pre-selected structure, each complex being designated a morphatide, said method comprising: (a) preparing a library of morphatides, comprised of: (i) a scaffolding component selected from the group consisting of nucleic acid, nucleic acid like molecule or nucleic acid analog having one or more regions of randomized sequence; and (ii) one or more agent molecules or type of agent molecules, associated, bound or bonded to the scaffolding component; (b) screening the library of morphatides prepared in step (a) by contacting, binding, or associating the morphatides with one or more suitable target molecules upon which a morphatide performs a preselected or desired function or to which a morphatide binds or associates through a pre-selected structure of said morphatide under conditions permitting said morphatide to perform said preselected or desired function on said target molecules or permitting said morphatide to bind or associate with said target molecules through the preselected structure; (c) separating the morphatides performing the preselected or desired function or binding or associating through the preselected structure, from the library of morphatides and target molecules; thereby identifying one or more complexes from a library of complexes, wherein said complex or complexes are selected for their ability to perform a preselected or desired function on a target molecule or by having a pre-selected structure.

The present invention further provides a method of identifying a presence of a substance in a sample from a subject, comprising: (a) obtaining a sample; (b) contacting the sample with one or more types of morphatide identified by either of the methods for identifying one or more complexes so as to form a complex between the morphatide and the substance present in the sample; (c) detecting the complex formed in step (b), thereby identifying the presence of the substance in the sample from the subject.

This invention further provides a method of diagnosing a subject wherein detection of a complex in step (c) of a method of identifying a presence of a substance in a sample is indicative of a disease.

Another aspect of the present invention provides a morphatide capable of effectively binding to, crosslinking with, or reacting with multiple types of molecules. Another aspect of the present invention provides a morphatide capable of effectively binding to, crosslinking with, or reacting with one type of molecule.

Still another aspect of the present invention provides a composition comprising the preferred embodiment of the morphatide effective to treat a subject and a pharmaceutically acceptable carrier.

The present invention further provides a morphatide labeled with a detectable marker.

This invention also provides a method of treating a subject with compositions of morphatides and morphatides conjugated to therapeutic agents.

In another aspect, this invention provides a method of drug delivery to a target in the body of a subject comprising administration to a subject any of the above-described compositions of morphatides and morphatides conjugated to therapeutic agents.

This invention further provides a method of drug delivery to a target in the body of a subject comprising administration to a subject of the above-described compositions of morphatides and morphatides conjugated to therapeutic agents, wherein the morphatide is incapable of being degraded or is slowly degraded after administration to the subject, thereby delivering the morphatide-bound drug to the target.

This invention still further provides a morphatide that is capable of binding to any component of an antibody molecule, said antibody having a constant and variable region.

BRIEF DESCRIPTION OF THE FIGURES

FIG. 4. Depicts the use of a particular type of bioconjugate, phenyl boronic acid, which can be used as a linker in the present method.

DETAILED DESCRIPTION OF THE INVENTION

Figure 1B:
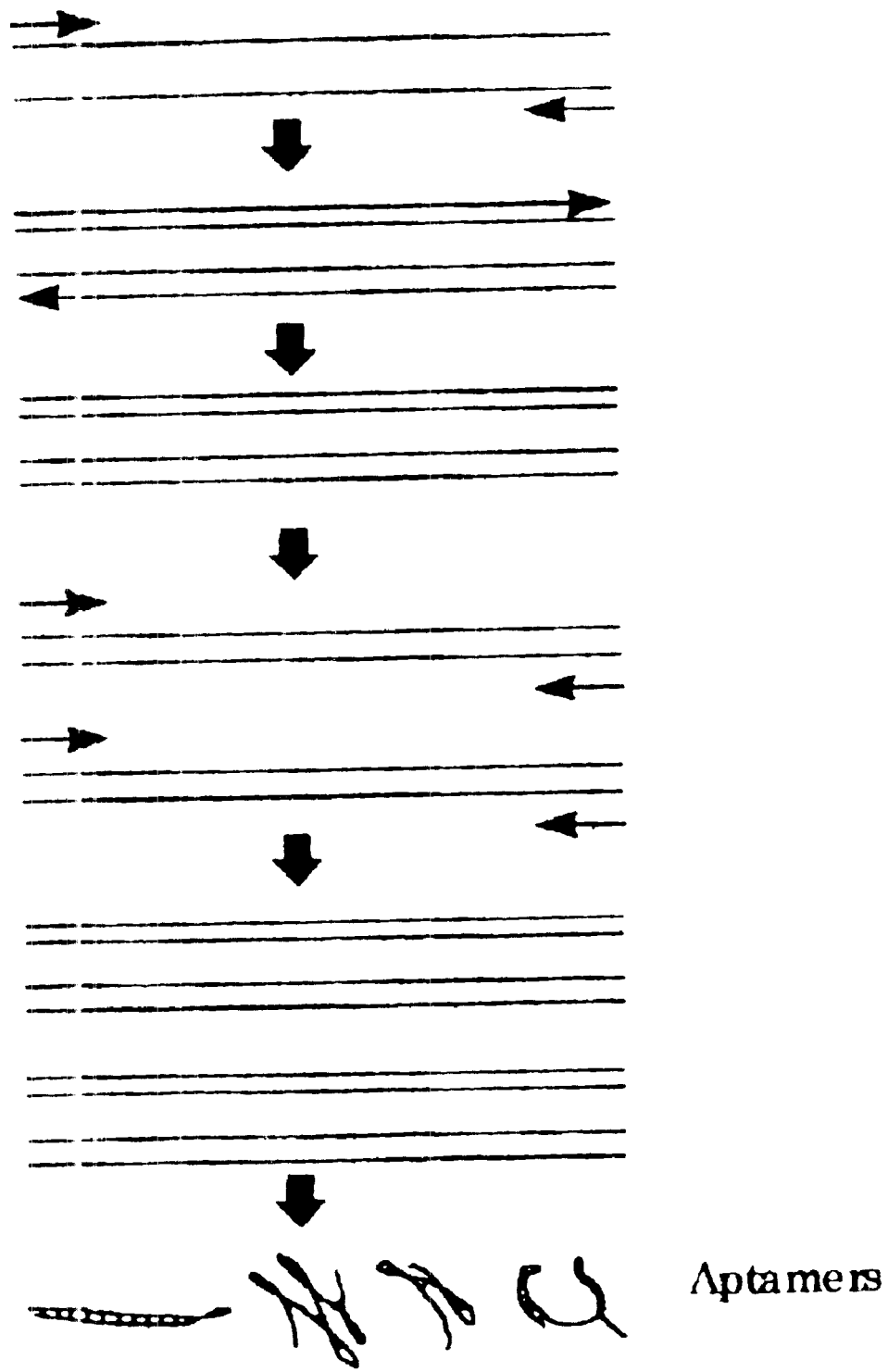
FIG. 1. Briefly demonstrates one well known strategy for generating and utilizing "Aptamers", a library of nucleotide shapes.

Unlike previously described technologies and methods, the present invention is an approach that maintains the facile ability of nucleic acids to evolve, while introducing the properties of additional components to create molecules with binding properties previously restricted to protein-like molecules. The basis of this invention is a Morphatide (previously termed "Morphotide"). A morphatide as used herein, is a complex comprised of a scaffolding component, hereinafter defined, one or more linker components, hereinafter defined, and one or more "agent" molecules hereinafter defined. Once desirable Morphatides are identified, scaffolding components can be separated from the agent molecules, evolved to generate a new, different and potentially better library of scaffolds, reconnected to the same or different agent molecules to generate a new library of Morphatides, and rescreened for an even more desirable activity of either the entire Morphatide or individual components thereof. This approach permits the directed evolution of polynucleotide molecules which can be disconnected, amplified and evolved. The present invention is thus an approach which couples the distinct advantage of the self replication of oligonucleotides and their potential to be evolved, with the richness of diversity of chemical modifications hitherto associated with other types of libraries.

In accordance with the present invention, libraries comprising structural or scaffolding components, linker molecules, and agent molecules are produced. Alternatively, the libraries may comprise structural or scaffolding components and agent molecules without linker molecules. Useful candidate compounds are identified from said shape and structure libraries. The useful candidate compounds can then be separated from the library and either modified to generate an even more useful candidate, or utilized directly.

The novel shapes and structures generated utilizing the present invention are named "Morphatides". The process of generating and screening a Morphatide library is deemed "Morphatide based combinatorial chemistry". Morphatide combinatorial chemistry can begin with a template scaffolding molecule. In one example, if this scaffolding molecule is a nucleic acid molecule, the molecule is amplified utilizing a process known as "sloppy PCR", "error-prone PCR" or "mutagenic PCR" (PCR Primer, A Laboratory Manual, Cold Spring Harbor Laboratory Press 1995) and nucleotides that have been coupled to, associated with, or attached to a component of a linker molecule or to a linker molecule. The nucleotides can be naturally occurring, novel or unique, or nucleotide analogs. "Error-prone, or sloppy or mutagenic, PCR" as a process for performing the polymerase chain reaction under conditions where the copying fidelity of the DNA polymerase is low, such that a high rate of point mutations is obtained along the entire length of the PCR product. This process generates various scaffolding molecules with components of linker molecules or linker molecules randomly attached throughout each molecule. Alternatively, nucleic acid scaffolding molecules (components) can be generated synthetically using techniques well known in the art by sequence randomization of individual nucleic acid bases utilizing naturally occurring nucleotides, novel or unique nucleotides, or nucleotide analogs. (Ecker, D. J. et al., 1993) Oligonucleotide synthesis a well characterized chemistry that can allow tight control of the composition of the mixtures of oligonucleotides created. Degenerate sequences can be readily produced. Association to linkers or to linker components can also occur after generation of scaffolding components. A library of Morphatides is then created by associating one or more agent molecules, which in one case have also been coupled or connected to other components of the linker molecule or not, with the scaffolding molecules to connect or associate the components of the linker molecules to each other or to connect or associate the agent molecule to the scaffold/linker mini-complex, thereby generating complexes (Morphatides) assembling the scaffolding molecules, linker molecules and the agent molecules. One can use mixtures of "agent" molecules attached to one type of linker/scaffold attachment site with the present invention. This library is screened to enrich or select for any desired interaction (typically a binding event) with any target (substrate or substrates) of interest. Novel shape and structure libraries, i.e., morphatides, identified by the methods of screening provided by the present invention are thereby generated. Subsequent to screening, Morphatides may be utilized directly, scaffolding and/or agent molecules and/or complex molecules may be analyzed and mimics of either the entire Morphatide or components thereof may be created for further use, or components of the Morphatides (agent, linker and scaffolding molecules) may be separated, modified, new Morphatides generated and the entire process repeated (iterative selection process). Once a morphatide or collection of morphatides have been identified via the screening process, the structure of one or more of the complexes (morphatides) can be analyzed to retrieve information in order to allow the generation or creation of chemical or small organic molecules that mimic the selected or desired morphatide. Alternatively, the components of the selected morphatide or collection of morphatides can be separated and the scaffolding component "evolved" utilizing any of the (error prone or sexual PCR or random or directed mutagenesis techniques well known to one of ordinary skill in the art. This process is demonstrated in FIGS. 2(a) and 2(b) and FIG. 3.

Interaction of selected Morphatides and target molecules can occur via binding, contact, connection or other association between the entire complex (Morphatide) and the target, or between any portion of the Morphatide and the target. Each component of the Morphatide can contribute to the shape, structure and/or function of the Morphatide, however actual interaction with a target can occur between any one or more of the components and the target. For instance, any individual component, such as the scaffolding component, linker component, or agent molecule can be the site for binding or associating with the target, or any combination thereof, such as the scaffolding component and the linker component, or the scaffolding component and the agent molecule, etc. can contribute to the binding or association. After desirable Morphatides are identified using the method described, one can further select even more desirable Morphatides by utilizing sexual PCR to effectively eliminate portions of selected Morphatides that do not contribute to the binding or interaction with the target. Sexual PCR, also known as DNA shuffling (U.S. Pat. No. 5,605,793, entitled "Methods for In-vitro Recombination", Feb. 25, 1997) is employed utilizing modified scaffolding components of the selected Morphatides and similar non-modified scaffolding components to generate further optimized Morphatides. In this process, scaffolding components with attached linkers or linker components of previously identified Morphatides are first separated from the agent molecules and combined with scaffolding components having the same nucleic acid sequence, however not being associated with linkers or linker components. The DNA is then fragmented and reassembled using the sexual PCR technique to generate new scaffolding molecules (components) which are very similar to the original scaffolding molecules, however different. Certain linker attachment sites in the newly generated scaffolding molecules may have been eliminated. Reattachment or association of agent molecules to generate another set of Morphatides can yield a further optimized Morphatide or Morphatides.

Figure 2A:
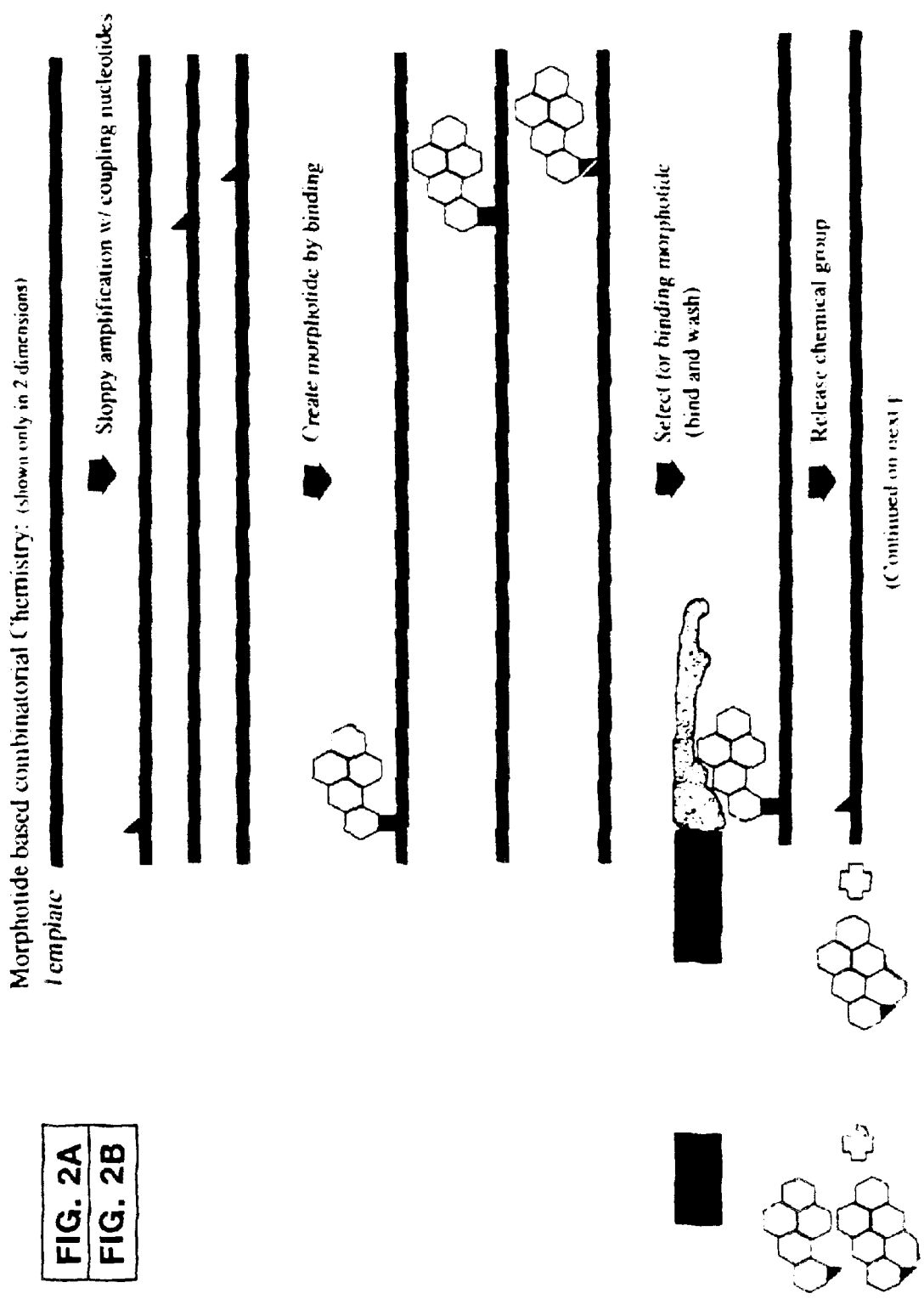
FIGS. 2A–B. Present an example of the method described in the present invention beginning with a template nucleic acid molecule as the scaffolding molecule.
Figure 2B:
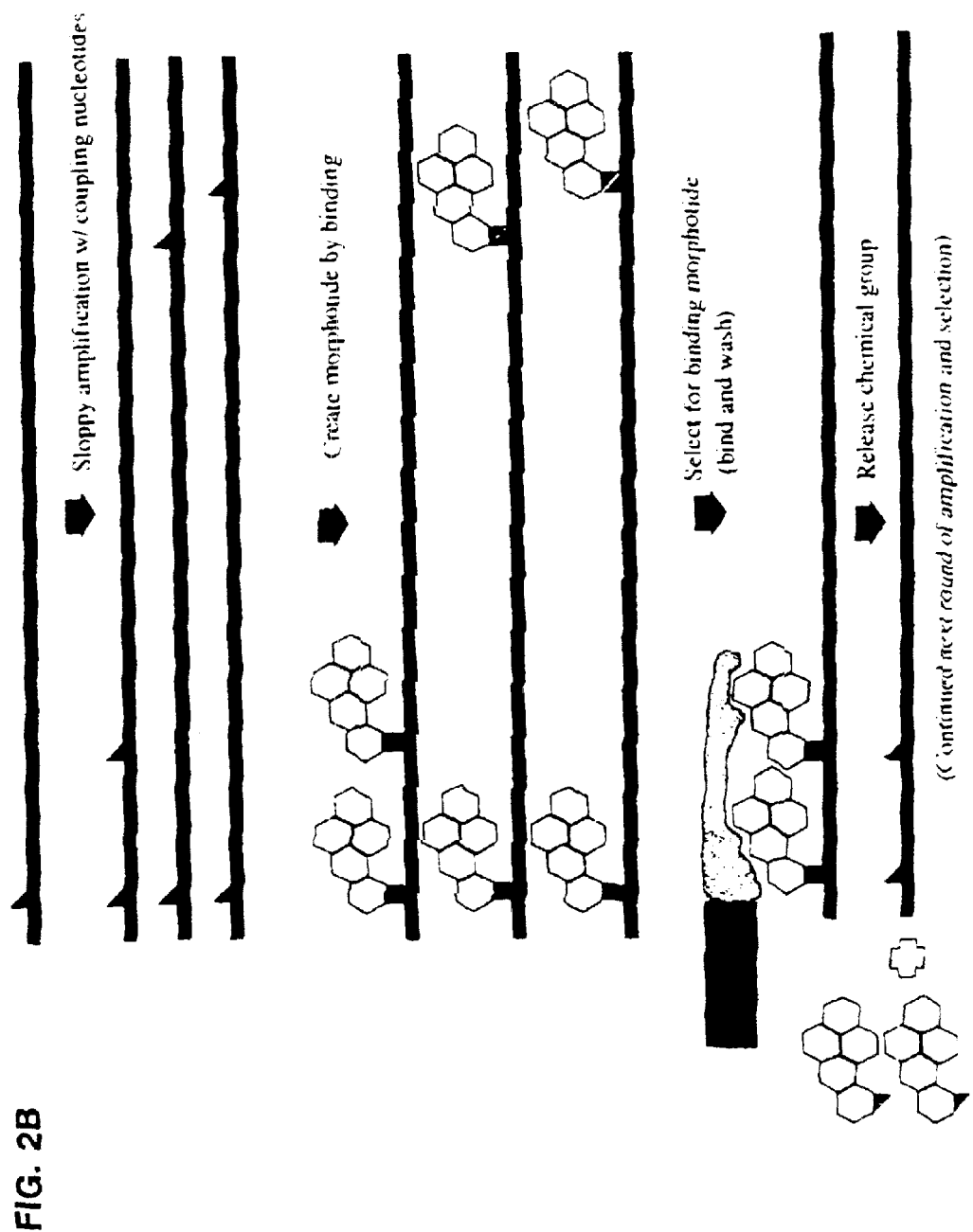

In FIGS. 2(a) and 2(b), an example of the process begins with a template nucleic acid molecule. The template is amplified in the presence of nucleotides which have been previously associated with linker components ("coupling nucleotides"), generating scaffolding molecules. The amplification is performed under conditions to allow random incorporation of the coupling nucleotides. Morphatides are created by, in this example, binding the scaffolding molecules to agent molecules, in this example, chemicals. As used herein, "chemicals", include but are not limited to molecules with aliphatic, aromatic, carboxyl, hydroxyl or amine groups. Binding, or desired Morphatides, are selected for by binding to a substrate of interest, and a wash step is used to remove all non-binding substrates and/or Morphatides. In this example, the substrate is then separated from the Morphatide, the chemical group is released. The enriched or selected for scaffolding molecule(s) are then subjected to amplification under conditions which allow for random incorporation of coupling nucleotides, again, and the process continues as before until the desired Morphatide or collection of Morphatides is finally determined or recovered.

Figure 3A:
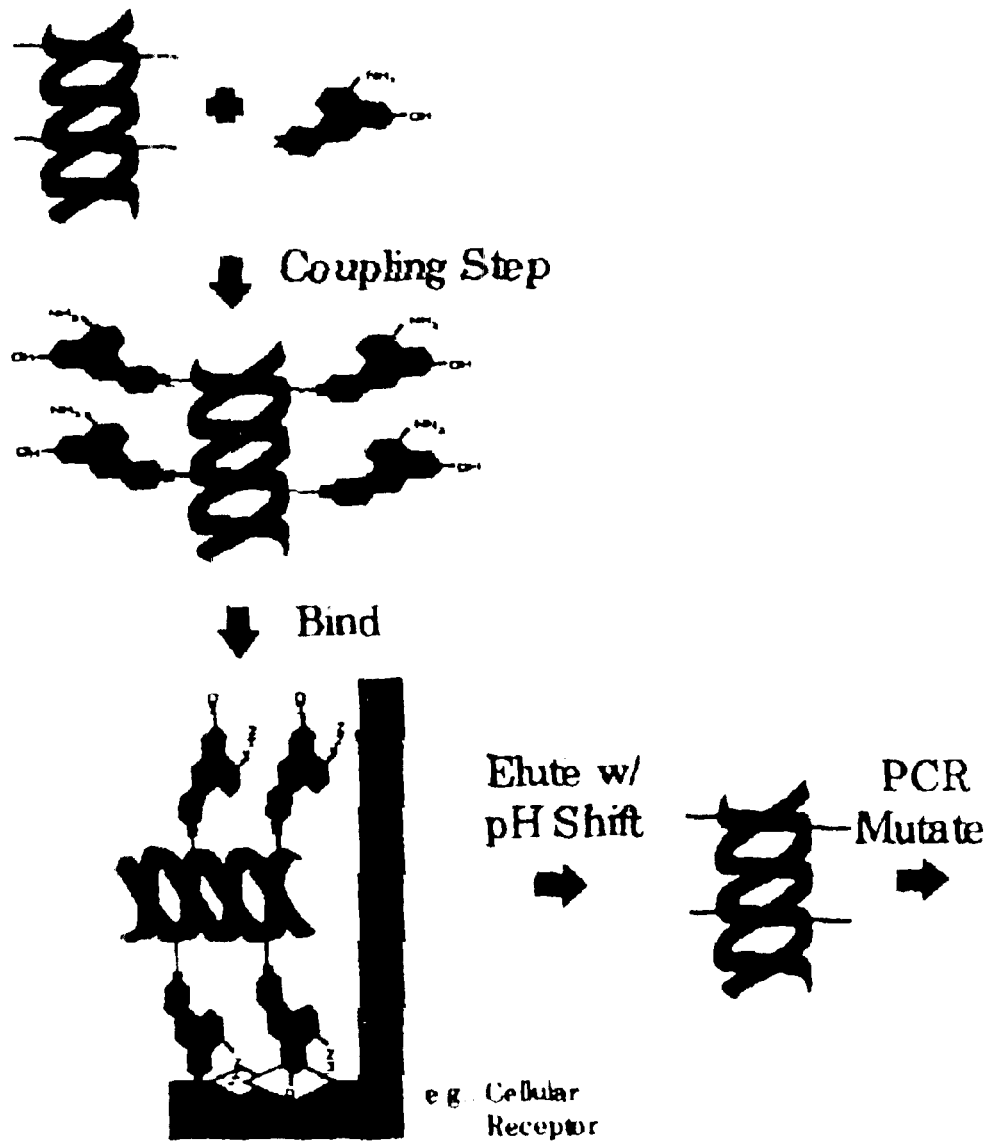
FIG. 3. Depicts a similar example of the method described in the present invention, indicating the target molecules bound to a solid support, and the dissociation of the complex molecules from the target molecules occurring via elution with a pH shift.
Figure 3B:
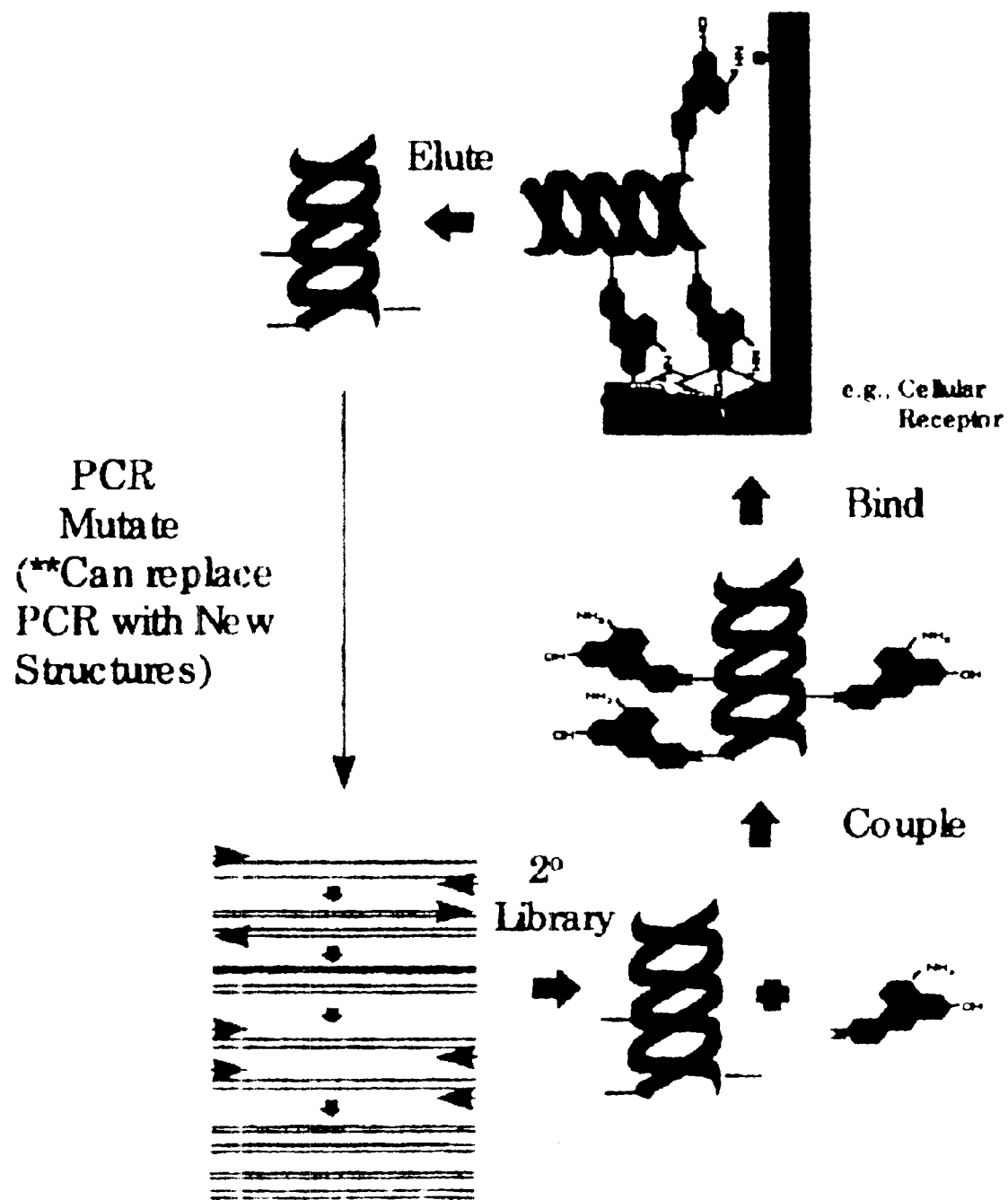

FIG. 3 depicts the process different format. In this example, the target (substrate) has also been immobilized to a solid surface, and the target (substrate) is separated from the Morphatide after the first screen by elution with a pH shift.

Variable scaffolding molecules can be generated or further modified utilizing a variety of techniques known in the art, including "sloppy", "error-prone" or "mutagenic" PCR, as mentioned. Another technique which may be employed is known as "sexual PCR". Sexual PCR is the forced homologous recombination between nucleic acid molecules of different but highly related sequences in vitro, caused by random fragmentation of the nucleic acid molecules, priming of the fragments on a non-parental nucleic acid molecule based on sequence homology, followed by fixation of the crossover by primer extensions in an amplification reaction. Sexual PCR is used for the in vitro evolution of DNA sequences. The libraries of recombinants that are created by sexual PCR are selected in vitro or in vivo for the best combinations of mutations at the nucleic acid, protein or metabolite level. The process of recombination, selection and amplification can be repeated for as many cycles as necessary to identify the best combinations. Once a collection of Morphatides has been enriched, components of the molecules can be separated from each other, and sexual PCR can be performed to create new scaffolding molecules. After reassociation, the newly generated Morphatides can be further enriched or screened for activity of interest.

Scaffolding molecules can also be generated or further modified by other mutagenic techniques such as cassette mutagenesis or site directed mutagenesis. Cassette mutagenesis is any process for replacing a small region of a double stranded DNA molecule with a synthetic oligonucleotide "cassette" that differs from the native sequence. The oligonucleotide often contains completely and/or partially randomized native sequence.

"Scaffolding components" of the present invention are molecules that contribute to the conformational diversity and contribute to the complexity of the morphatide libraries to be screened. Diverse scaffolding molecules allow each comp molecule in the library to have a distinct shape. "Shape" as been defined as "the net sum of all the molecule properties and dynamic features that would affect interaction (of molecules) with other molecules". (Kenan, D. J. et al. 1994) Nucleic acid scaffolding components of the present invention can also provide the capability to clone, amplify, and evolve components of the morphatides and to decode the structure of the selected morphatides.

Nucleic acid scaffolding molecules can consist of single stranded, double stranded, triple stranded or branched DNA or RNA molecules. DNA or RNA scaffolding molecules can be generated using synthetic or biosynthetic methods. Nucleotide analogs to nucleotide bases, such as 5-azo-cytodine, inosine or 7-deaza-guanine can be employed to increase the complexity of the resulting scaffolding molecules. Nucleotide bases may be modified prior to, or after, generation of nucleic acid scaffolding molecules. Nucleotide scaffolding molecules can be generated by randomization of the order of individual bases or modified bases. (Houghten, 1985; Beaudry and Joyce, 1992) Such techniques are well known to those skilled in the art.

Scaffolding molecules of the present invention can comprise a variable core flanked by short sequences to facilitate amplification. The variable core can be designed such that the sites of connection to the linker can be readily identified. This could facilitate the rapid determination of the structure of an optimized scaffolding molecule component of a Morphatide. For example, by constructing the variable core as follows, this challenge can be resolved: since a polynucleotide comprising just 3 of the 4 normal bases provides adequate variation for the scaffolding molecule, the remaining base can be used to serve as the connector or attachment site for the linker to carry the agent molecules. By having one base function as the attachment site for the linker in the construction of the variable core, the number of linker sites can be controlled and the position readily ascertained.

Alternatively, any one or more of the different bases or any base mimic can be used as an attachment site. Preferably, sites of connection of the linker and agent are internal in the scaffolding component to potentially provide greater shape and structural diversity. Connection sites restricted to terminal sites in the scaffolding components may limit this desired feature. It should be noted that if one were only utilizing a modified nucleotide to interact or bind to a target of interest, internal connection or modified sites could severely interfere with any further hybridization event of this nucleotide. With the present invention, however, the greatest shape and structural diversity can be provided by utilizing internal sites of the scaffolding molecules for connection.

It is recognized that novel, or unique bases or base analogs, not included in the 4 normal bases, can be employed in the present invention. Such novel or unique bases or base analogs can include, but are not limited to, bases, base analogs or "mimics" such as difluorotoluene deoxynucleosides, (Rawls, R., 1997) or other molecules which can be incorporated by any nucleic acid polymerase to any degree, and/or which do or do not effect hybridization, binding or association of a nucleotide to any other molecule or molecules.

It is also recognized that more than one nucleic acid polymerase can be employed simultaneously to incorporate bases or base analogs and/or "linker" attached bases or base analogs.

Scaffolding molecules can also be modified post generation via a variety of chemical techniques, such as that employed in the Maxam and Gilbert DNA sequencing procedure, or via the utilization of known mutagens such as UV light, or DNA binding proteins which can cause modifications to specific or random nucleotides. The Maxam and Gilbert DNA sequencing procedure is very well known in the art. (Maxam, A. M. and Gilbert, W. 1980) The procedure involves the treatment of DNA samples with a chemical that specifically damages or modifies one or two of the four bases in DNA in a controlled reaction where only a few of the sites are nicked in any one DNA molecule. The chemicals utilized in this procedure can be utilized in the present invention. Mutatable nucleotides, such as methylated cytosines may be utilized to generate scaffolding molecules. Mutagens such as (+)-CC-1065; (+)-CC-1065 (N3-Adenine); trivalent chromium or trivalent chromium salts; polycyclic aromatic hydrocarbons (PAH), such as 7-bromomethyl-benz[a] anthracene (BMA); Tris(2,3-dibromo-propyl)phosphate (Tris-BP); 1,2-dibromo-3-chloro-propane ("DBCP"); 2-bromoacrolein (2BA); benzo[a]pyrene-7,8-dihydrodiol-9-10-3epoxide (BPDE); platinum(II) halogen salts; N-hydroxy-2-amino-3-methyl-imidazo[4,5-f]-quinoline (N-hydroxy-]Q); or N-hydroxy-2-amino-1-methyl-6-phenylimidazo[4,5-f]-pyridine (N-hydroxy-Ph]P) can be added to modify nucleic acids by adding chemical adducts to specific or random nucleotides. These adducts or adducted sites may then be utilized as linkers to which agent molecules, hereinafter defined, can be attached, or can themselves act as agent molecules.

"Agent molecules" of the present invention are molecules that further provide for complex and diverse morphatides. As used herein, an agent molecule is a molecule that can be recognized by or can recognize a particular target molecule or portion of a target molecule of interest. This recognition is typically a binding event or some other event of association. Screening of and selection from shape and structure libraries (Morphatides) represents an approach to generating complexes of molecules that recognize and bind target molecules. The molecules that recognize and bind target molecules may be the entire complex of molecules (the Morphatides) or individual components thereof, including but not limited to the agent molecules or the scaffolding components.

"Agent molecules" can consist of natural products such as natural polymers (peptides, oligonucleotides, etc.) or natural nonpolymeric molecules (antibodies, etc.), or of unnatural products such as synthetic polymers or other synthesized nonpolymeric molecules. Examples of agent molecules include, but are not limited to, peptides, nucleic acids, carbohydrates, proteins, and other molecules synthetic compounds, agonists and antagonists for cell receptors, hormones, chemicals, chemical structures, sugars, cofactors, enzymes and other proteins, enzyme substrates, and drugs. There are virtually an unlimited number of agent molecules that may be screened using the present invention. Assembly of agent molecules can occur by systematic association of building block components of agent molecules using chemical, biological, or biosynthetic procedures.

Synthesis methods are well known in the art. Building block components of agent molecules can be diverse and fairly complex. Assembly of such building blocks could yield a broad, diverse collection of agent molecules providing diverse physicochemical properties, functionality, charge, and conformation. Building blocks could have groups with high reactive functionality that allow for multiple new covalent combinations and many potential connecting permutations providing diverse, spatial relationships (carbohydrates, for example, where almost every carbon in a given molecule has a hydroxyl or other oxygen-containing functional group attached to it)

"Linker molecules" of the present invention are molecules that can allow connection or association of the scaffolding molecules to agent molecules. Linker molecules can consist of chemical compounds. Typically, the chemical compounds contain one or more reactive groups, allowing the linkers to associate and preferentially to be cleaved or disconnected by means of a specific reaction or reaction steps. Linkers also have appropriate functional groups at each end for coupling to the scaffolding molecules and to the agent molecules. Preferred linkers are those whose cleavage or disconnection is controllable. Particularly preferred linkers are those whose cleavage or disconnection is reversible. Illustrative examples of suitable linkers include bioconjugates such as Phenylboronic Acid, DNA binding proteins, or biotin/streptavidin. In addition to the cleavable groups, suitable linkers may contain other groups that influence or do not influence the cleavage reaction, which are suitable for enriching or separating scaffolding molecules from agent molecules.

"Cleavable linkers" may also consist of a cleavable component and a constant component, which is the same for either all scaffolding molecules or for all agent molecules. The constant part may consist of chemical compounds which permit attachment to both the cleavable part of the linker and to other chemical groups or to other molecules. An example of a constant component is an invariable part of the scaffolding molecule or of the agent molecules.

Nucleotide molecules can be used alone as scaffolding molecules, or linker molecules can be employed in the present invention to force the shape of the resulting complex molecules to yield novel shapes, or scaffolding molecules.

There are a variety of linkers that may be useful for purposes of the present invention. For instance, linker molecules could be based upon the phenylboronic acid complexing moieties (Yurkevich 1969). Phenylboronic acids are known to interact with a wide range of polar molecules having the requisite functionalities (Middle 1983; Frantzen 1995). Phenylboronic acid, like boric acid, is a Lewis acid, and ionizes not by direct deprotonation, but by hydration to yield the tetrahedral phenylboronate anion (pKa=8.86). A variety of phenylboronic acid molecules with varying pKa's are commercially available. Molecular variations can also be generated. Ionization is fundamental for complexation causing a change from trigonal coordination to tetrahedral coordination. Bioconjugation with phenylboronic acid molecules has been achieved between compounds having diol functionalities (e.g. carbohydrates) to immobilized phenylboronate anion to form cyclic esters under alkaline conditions. Release is effected by pH shifts. Phenylboronic acid modified dUTP linker molecules have also been incorporated into oligomers using DNA polymerases as an alternative to DNA labeling and purification via biotin incorporation. Bioconjugation via linkers such as the phenylboronic acid linker can simplify the reversibility of the coupling reaction, enabling attachment of agent groups that cannot generally be incorporated by DNA polymerases. In addition, the phenylboronic acid molecule causes minimal interference with respect to DNA hybridization and base incorporation with a deoxynucleotide triphosphate attached to it.

Phenylboronic acid bioconjugate complex is suitable to be used as a linker molecule in the present invention. It is a preferred embodiment. Methods for associating and dissociating suitable linkers to many different types of potential molecules, such as the agent molecules and/or scaffolding molecules referred to in the present invention are known to one of ordinary skill in the art. (WO 95/20591) These methods include but are not limited to those described in WO 95/20591, as well as those using biotin-streptavidin. FIG. 4 depicts the use of this type of candidate bioconjugate, indicating the fact that standard chemistry can be used to attach one component of the bioconjugate (linker) to candidate scaffolding molecules (Binder 1 or 2), and to attach another component of the linker to candidate agent molecules (Binder 2 or 1, depending on which Binder scaffolding molecule is). A condensation reaction then associates the linker components, creating a complex, or Morphatide.

As used herein a binder is any molecule which is to be attached to another molecule by the linker. Binders include but are not limited to nucleic acids, amino acids and chemical groups. Therefore, the components of a Morphatide, i.e., the scaffolding component and the agent molecules are binders.

Linkers can be coupled via functional groups to one or more different sites on both scaffold molecules and agent molecules. Synthesis methods to attach phenylboronic acid to other molecules are known (WO 95/20591). Connecting scaffold molecules to agent molecules via a reversibly connectable linker such as phenylboronic acid yields conformationally diverse library complex molecules.

"Target molecules" of the present invention are molecules to which morphatides are selected to bind, associate, or interact. Target molecules can be any molecule of interest. Examples of such molecules include, but are not limited to, cell membrane receptors, antibodies, lectins, polysaccharides, cells, cellular membranes, organelles, and chemicals. Preferably, target molecules of interest are bound to a support. Examples of such supports include, but are not limited to, solid surfaces, beads, particles, or other support.

Libraries of complexes (morphatides) can be screened for any target molecule of interest or any biological activity of interest which may be known in the art. Biological activities known in the art include, but are not limited to, antimicrobial activities, antitumor activities, enzyme inhibiting activities, receptor binding activities, growth promotion activities, antibody binding activities and biofilms. Many screening assays are available and known for these activities and a variety of other biological responses, and any can be used with the present invention.

Evolution via such techniques as previously described, such as Sexual PCR, may be performed on undesirable scaffolding molecules subsequent to identification and separation from desirable complexes to eventually create new collections of complexes which can be rescreened for desirable activity. Undesirable scaffolding molecules are those scaffolding molecules that are part of the Morphatides that do not bind or "pass" the screening test.

A variety of screening techniques are known in the art and can be used in the present invention. (Mullinax, R., et. al., 1990; Barbas, C., et. al., 1991; Castagnoli, L., et. al., 1991; Garrard, L., et. al., 1991; McCafferty, J., et. al., 1990; Clackson, T., et. al., 1991; Kang, A., et. al., 1991; Hoogenboom, H., et. al., 1991; Chang, C., et. al., 1991;).

It is recognized that with any screening technique involving a binding event, steps may be taken to decrease potential non-specific binding of Morphatides. These steps are well known in the art, and include but are not limited to enriching, isolating or separating bound or otherwise associated complexes from unbound or unassociated complexes can occur via a variety of enrichment, isolation and separation techniques well known in the art. Typical enrichment, isolation and separation techniques involve solvent partitioning and/or conventional chromatography.

Enriching, isolating or separating bound complexes (morphatides) from target molecules can occur via a variety of isolation and separation techniques, also well known in the art, and depend on the nature of the connection between the complex and the target molecule. Typical enrichment, isolation and separation strategies involve elution or digestion steps.

More particularly, the present invention provides a method for identifying one or more complexes from a library of complexes, wherein said complex or complexes are selected for their ability to perform a preselected or desired function on a target molecule or by having a preselected structure, each complex being designated a morphatide, said method comprising: (a) preparing a library of morphatides, comprised of: (i) a scaffolding component selected from the group consisting of nucleic acid, nucleic acid like molecule or nucleic acid analog having one or more regions of randomized sequence; (ii) one or more linker components; and (iii) one or more agent molecules or type of agent molecules, linked to the scaffolding component by one or more type of linker components; and (b) screening the library of morphatides prepared in step (a) by contacting, binding, or associating the morphatides with one or more suitable target molecules upon which a morphatide performs a preselected or desired function or to which a morphatide binds or associates through a pre-selected structure of said morphatide under conditions permitting said morphatide to perform said preselected or desired function on said target molecules or permitting said morphatide to bind or associate with said target molecules through the preselected structure; (c) separating the morphatides performing the preselected or desired function or binding or associating through the preselected structure, from the library of morphatides and target molecules; thereby identifying one or more complexes from a library of complexes, wherein said complex or complexes are selected for their ability to perform a preselected or desired function on a target molecule or by having a pre-selected structure.

Another aspect of the present invention provides a method for identifying one or more complexes from a library of complexes, wherein said complex or complexes are selected for their ability to perform a preselected or desired function on a target molecule or by having a pre-selected structure, each complex being designated a morphatide, said method comprising: (a) preparing a library of morphatides, comprised of: (i) a scaffolding component selected from the group consisting of nucleic acid, nucleic acid like molecule or nucleic acid analog having one or more regions of randomized sequence; and (ii) one or more agent molecules or type of agent molecules, associated, bound, or bonded to the scaffolding component; (b) screening the library of morphatides prepared in step (a) by contacting, binding, or associating the morphatides with one or more suitable target molecules upon which a morphatide performs a preselected or desired function or to which a morphatide binds or associates through a pre-selected structure of said morphatide under conditions permitting said morphatide to perform said preselected or desired function on said target molecules or permitting said morphatide to bind or associate with said target molecules through the preselected structure; (c) separating the morphatides performing the preselected or desired function or binding or associating through the preselected structure, from the library of morphatides and target molecules; thereby identifying one or more complexes from a library of complexes, wherein said complex or complexes are selected for their ability to perform a preselected or desired function on a target molecule or by having a preselected structure.

The contacting, binding, or associating of the morphatides to target molecule(s) or of a morphatide conjugated to a therapeutic agent(s), as described infra, may be through ionic, covalent, hydrophobic or hydrogen bonds, or through Van der Waals forces.

In an embodiment of the above-described methods, the separation of step (c) is performed by either (a) separating the morphatides which do not perform the preselected or desired function or which do not bind or associate through a pre-selected structure or (b) separating the morphatides which perform the preselected or desired function or which bind or associate through a pre-selected structure.

Methods of separating are well known to one of ordinary skill in the art and include but are not limited to centrifugation; electrophoresis; biopanning; solubility differences; chromatography; fluorescence sorting, properties such as physical, chemical or electrical; photochemical; magnetic; and visible detection.

In a preferred embodiment of the above-described methods said target molecule is bound to a solid support. In a preferred embodiment the preselected or desired function performed by the complex(es) on a target molecule is selected from the group consisting of binding to or associating with said target molecule; reacting with said target molecule and changing the property of said target molecule; having an affinity for and binding to a specific ligand; performance of a biological activity, wherein said biological activity is selected from the group consisting of antimicrobial activity, antitumor activity, enzyme inhibiting activity, enzyme enhancing activity, receptor binding activity, growth promotion activity, antibody binding activity; formation of a biofilm; enzymatic activity, immune modulating activity, cell signaling activity, polymerizing activity, and encapsulating activity.

In another embodiment the contacting, binding or association is selected from the group consisting of multiple complexes acting on a single target molecule, a single complex acting on multiple target molecules, components of one or more complexes acting on multiple target molecules, components of one or more complexes acting on a single target molecule, and multiple complexes acting on multiple target molecules.

In a preferred embodiment the scaffolding component comprises naturally occurring nucleotides, novel or unique bases, base analogs or any combination thereof. In an embodiment said scaffolding component comprises synthetically generated nucleic acids, nucleic acid like molecules, nucleic acid analogs. In an embodiment the nucleic acid like molecule is a difluorotoluene or related deoxynucleoside.

In another embodiment of the above-described methods said scaffolding component consists of subunits which are capable of being incorporated by one or more nucleic acid polymerases or reverse transcriptases and which can, when polymerized, generate hybridizable polymers with hydrogen bonding or hybridizable polymers without hydrogen bonding. In another embodiment said scaffolding component comprises nucleic acids having regions of conserved sequences and one or more regions of randomized sequences. In a preferred embodiment the scaffolding component(s) are comprised of two fixed regions of nucleotides and one region of randomized nucleotides between the two fixed regions. In an embodiment the linker component is associated to a base of the scaffolding component either before or after the scaffolding component is made. In another embodiment the randomized region is comprised of: (a) three of the four bases occurring with similar frequency; and (b) one of the four bases occurring at a rare frequency. In an embodiment one of the bases occurring with similar frequency is associated with or binds with the linker component. In an embodiment one of the four bases occurring at a rare frequency is associated with or binds with the linker component. In an embodiment the position of the base with the linker attached is determined by nucleotide sequencing or mass spectrophotometry.

In another embodiment each scaffolding component comprises more than one different nucleic acid base being attached to a linker component, said nucleic acid base being incorporated into the scaffolding component either during PCR amplification or during synthesis of the nucleic acids. In an embodiment the incorporated nucleic acid base to which the linker component is attached is a rare base. In an embodiment, base to which the linker is attached is modified, said modification being by chemical reaction either before or after incorporation during PCR amplification or during synthesis of the nucleic acids.

In further embodiment the incorporated nucleic acid base to which the linker component is attached is a different modified base, said base being any of the four bases or analogs of said bases, said base being modified by a reaction. In a preferred embodiment the incorporated base to which the linker component is attached is located internally in the scaffolding component.

In a further preferred embodiment one or more of said linker components are reversible. In an embodiment one or more of said linker components are non-reversible. In an embodiment one or more of said linker components cannot be amplified (any kind of mathematical increase in the number of molecules) in vitro or in vivo. In another embodiment one or more of said scaffolding components associated with one or more of said linker components is amplifiable in vitro or in vivo. In an embodiment said one or more of said linker components associated with one or more of said agent molecules cannot be amplified in vitro or in vivo. In a preferred embodiment the entire morphatide is amplifiable. In a further preferred embodiment one or more of said linker components comprise reversibly connectable components or parts.

In an embodiment a first linker component either reversibly or non-reversibly associated with a scaffolding component and a second linker component either reversibly or non-reversibly associated with an agent molecule are connected together to generate a scaffolding component linked to an agent molecule by the connectable first and second components of said linker component. In a preferred embodiment the linker component is selected from the group consisting of a phenyl-boronic acid linker, a thio linker, and a biotin-streptavidin linker. In an embodiment the thio linker is cysteine. In another embodiment the scaffolding component is associated to one or more agent molecules, wherein said agent molecule is a peptide by a peptide bond. In an embodiment the linker component is selected from the group cola nucleic acid binding protein and a chelating molecule. In an embodiment the linker component is bound covalently to either the scaffolding component or to the agent molecule. In another embodiment the linker component is bound noncovalently to either the scaffolding component or to the agent molecule. In an embodiment of the above-described methods said agent molecules are selected from the group consisting of naturally occurring polymers, synthetically generated polymers, and non-polymeric molecules.

In another embodiment of the above-described methods the library of complexes is prepared by: (a) coupling the linker molecules or components of the linker molecules to either the scaffolding components, to form scaffolding component-linker molecules or to the agent molecules, to form agent molecule-linker molecules; and (b) generating a linkage between the scaffolding component-linker molecules and the agent molecules or between the scaffolding components and the agent molecule-linker molecules to yield the complexes, thereby preparing a library of complexes. In an embodiment said scaffolding components are prepared for coupling to linker molecules via chemical reaction yielding modified nucleotides. In a further embodiment said chemical reaction involves treating the scaffolding components with one or more mutagens to add one or more base specific or non-specific adduct(s), resulting in adducted scaffolding molecules, that enable increased reactivity of the base to the linker or directly to the agent molecules. In a still further embodiment said chemical reaction involves treating the scaffolding components with one or more mutagens to add one or more base specific or non-specific adduct(s), resulting in adducted scaffolding molecules, said adduct acting as either a linker or an agent molecule. In another embodiment the adducted scaffolding components are amplifiable. In a preferred embodiment said mutagen is UV light, any other nucleic acid mutagen, or a nucleic acid binding protein. In a further preferred embodiment said chemical reaction involves treating scaffolding components with Maxam & Gilbert based chemistries to generate increased reactivity of one or more bases to a linker or to an agent molecules. In another embodiment said scaffolding components are prepared for coupling to the linker molecules via a non-chemical reaction yielding modified nucleotides. In an embodiment said non-chemical reaction is an enzymatic reaction.

In further embodiment of the above-described methods said methods further comprise after step (b): (a) disassociating the scaffolding component of the complex performing the preselected or desired function from the agent molecule or molecules; (b) generating modified scaffolding components; (c) associating the different scaffolding molecules with agent molecules to generate different morphatides; (d) rescreening the different morphatides by repeating steps (b) and (c) of claims 1 or 2 to identify new desired candidate morphatides.

In an embodiment said modification of the scaffolding components occurs via a random or directed mutagenesis technique. In an embodiment said random or directed mutagenesis techniques are selected from the group consisting of error-prone PCR or sexual PCR by performing a suitable number of cycles on the scaffolding components, resulting in one or more base changes in some percentage of the scaffolding components; cassette mutagenesis; and site directed mutagenesis. Such techniques are well known to one of ordinary skill in the art. One example of a random mutagenesis technique is termed "PCR mutagenesis". (PCR Primer, A Laboratory Manual, Cold Spring Harbor Laboratory Press 1995) Another mutagenesis technique, previously mentioned, is termed "DNA shuffling" or "Sexual PCR" (W. P. C. Stemmer, 1994) Another mutagenesis technique known to one of ordinary skill in the art is "Combinatorial Multiple Cassette Mutagenesis". [Biotechniques, (1995)] In vitro evolution procedures of nucleic acids have also been described by several other groups over the last many years. (A. Beaudry and G. Joyce).

In another embodiment one or more of said agent molecules in step (c) are different from the agent molecules utilized in the morphatides of the prior round of screening for identification of morphatides performing the preselected or desired function.

In another embodiment of the above-described methods for identifying a different morphatide further comprising: (a) separating the scaffolding components from the agent molecules: (b) performing a suitable number of cycles of error prone PCR on the scaffolding components, resulting in one or more base changes in some percentage of the scaffolding components; (c) reconnecting the scaffold component to the agent component; and (d) repeating steps (a) through (d) of the above-described methods, thereby identifying a different morphatide. In an embodiment the morphatide comprises a linker component, wherein in step (a) one part of a linker remains attached to the scaffold component and another part of the linker remains attached to the agent molecule. In another embodiment in step (c) both parts of the linker are connected, thereby reconnecting the scaffold component to the agent component. In a further embodiment the connection between the agent molecule and the scaffolding component is by a plurality of the linker component, i.e., pieces of the linker component. In an embodiment the scaffolding components are characterized by cloning and nucleotide sequencing before reattachment of the agent molecule in step (c).

A further embodiment of the above-described methods comprises (a) creating a mimic of the identified morphatide; and (b) using the mimic for a desired application.

In a still further embodiment the above-described methods further comprise: (a) separating scaffolding components with attached linker components or parts of the linker components from the agent molecules of the previously identified Morphatides; (b) combining the scaffolding components with attached linker components or parts thereof with scaffolding components comprising a same nucleic acid sequence as the scaffolding components, said nucleic acid sequence not being attached to or associated with a linker components or parts thereof, thereby resulting in nucleic acid sequences without the one or more linker sites; (c) using sexual PCR to fragment and reassemble the nucleic acid sequences, resulting in elimination of linker component sites which do not contribute to the binding of the morphatide, thereby generating new scaffolding components similar but not identical to the scaffolding components of step (a); (d) reattaching or association agent molecules to the new scaffolding components of step (c), thereby generating another set of Morphatides.

Yet another aspect of the present invention provides a method of identifying a presence of a substance in a sample from a subject, comprising: (a) obtaining a sample; (b) contacting the sample with one or more types of morphatide identified by either of the methods for identifying one or more complexes so as to form a complex between the morphatide and the substance present in the sample; (c) detecting the complex formed in step (b), thereby identifying the presence of the substance in the sample from the subject. In an embodiment step (c) is performed by PCR amplification, ethidium bromide staining or labeling selected from the group consisting of radioactive isotope, enzyme, dye, biotin, a fluorescent label, a chemiluminescent label and a ligand. In a preferred embodiment the detection of the complex formed in step (c) comprises identification of an occurrence selected from the group consisting of binding to or associating with a target molecule; having an affinity for and binding to a specific ligand; performance of a biological activity, wherein said biological activity is selected from the group consisting of antimicrobial activity, antitumor activity, enzyme inhibiting activity, enzyme enhancing activity, receptor binding activity, growth promotion activity, antibody binding activity; formation of a biofilm; enzymatic activity, immune modulating activity, cell signaling activity, polymerizing activity, and encapsulating activity.

This invention further provides a method of diagnosing a subject wherein detection of a complex in step (c) of a method of identifying a presence of a substance in a sample is indicative of a disease. In an embodiment the sample is a body fluid or a tissue specimen. In another embodiment the body fluid is selected from the group consisting of blood, serum, plasma, urine, saliva, nasal mucosal discharge, vaginal mucosal discharge, anal mucosal discharge, peritoneal fluid, cerebro-spinal fluid, and lymphatic fluid. In a further embodiment the substance whose presence is identified is selected from the group consisting of hormones, enzymes, proteins, cancer/tumor cells, pathogens, and drugs. In a still further embodiment the subject is bacterial cells, a plant, a microbe, an insect, a fish, or a mammal. In a preferred further embodiment the mammal is a human.

Still another aspect of the present invention provides a morphatide capable of effectively binding to, crosslinking with, or reacting with multiple types of molecules. Another aspect of the present invention provides a morphatide capable of effectively binding to, crosslinking with, or reacting with one type of molecule. In a preferred embodiment of the morphatide the binding to, crosslinking with, or reacting with the molecules is selected from the group consisting of binding to or associating with a target molecule; having an affinity for and binding to a specific ligand; performance of a biological activity, wherein said biological activity is selected from the group consisting of antimicrobial activity, antitumor activity, enzyme inhibiting activity, enzyme enhancing activity, receptor binding activity, growth promotion activity, antibody binding activity; formation of a biofilm; enzymatic activity, immune modulating activity, cell signaling activity, polymerizing activity, and encapsulating activity.

This invention provides a composition comprising the preferred embodiment of the morphatide effective to treat a subject and a pharmaceutically acceptable carrier.

This invention also provides a method of administering a the above-described compositions, wherein the administration is intravenous, intraperitoneal, intrathecal, intralymphatical, intramuscular, intralesional, parenteral, epidural, subcutaneous; by infusion, liposome-mediated delivery, aerosol delivery; topical, oral, nasal, anal, ocular or otic delivery. In a preferred embodiment the morphatide is conjugated to a therapeutic agent. In an embodiment the therapeutic agent is a radioisotope, toxin, toxoid, or chemotherapeutic agent.

This invention further provides a composition comprising the above-described conjugated morphatide and a pharmaceutically acceptable carrier, wherein the morphatide is selected from either a morphatide which is capable of being degraded or a morphatide which is incapable of being degraded after administration to a subject.

The present invention also provides a pharmaceutical composition comprising a effective amount of the morphatides described above and a pharmaceutically acceptable carrier. In the subject invention an "effective amount" is any amount of an morphatide which, when administered to a subject suffering from a disease or abnormality against which the morphatides are effective, causes reduction, remission, or regression of the disease or abnormality. In the practice of this invention the "pharmaceutically acceptable carrier" is any physiological carrier known to those of ordinary skill in the art useful in formulating pharmaceutical compositions.

In one preferred embodiment the pharmaceutical carrier may be a liquid and the pharmaceutical composition would be in the form of a solution. In another equally preferred embodiment, the pharmaceutically acceptable carrier is a solid and the composition is in the form of a powder or tablet. In a further embodiment, the pharmaceutical carrier is a gel and the composition is in the form of a suppository or cream. In a further embodiment the compound may be formulated as a part of a pharmaceutically acceptable transdermal patch.

A solid carrier can include one or more substances which may also act as flavoring agents, lubricants, solubilizers, suspending agents, fillers, glidants, compression aids, binders or tablet-disintegrating agents; it can also be an encapsulating material. In powders, the carrier is a finely divided solid which is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, polyvinylpyrrolidine, low melting waxes and ion exchange resins.

Liquid carriers are used in preparing solutions, suspensions, emulsions, syrups, elixirs and pressurized compositions. The active ingredient can be dissolved or suspended in a pharmaceutically acceptable liquid carrier such as water, an organic solvent, a mixture of both or pharmaceutically acceptable oils or fats. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (partially containing additives as above, e.g. cellulose derivatives, preferably sodium carboxymethyl cellulose solution), alcohols (including monohydric alcohols and polyhydric alcohols, e.g. glycols) and their derivatives, and oils (e.g. fractionated coconut oil and arachis oil). For parenteral administration, the carrier can also be an oily ester such as ethyl oleate and isopropyl myristate. Sterile liquid carriers are useful in sterile liquid form compositions for parenteral administration. The liquid carrier for pressurized compositions can be halogenated hydrocarbon or other pharmaceutically acceptable propellent.

Liquid pharmaceutical compositions which are sterile solutions or suspensions can be utilized by for example, intramuscular, intrathecal, epidural, intraperitoneal or subcutaneous injection. Sterile solutions can also be administered intravenously. The compounds may be prepared as a sterile solid composition which may be dissolved or suspended at the time of administration using sterile water, saline, or other appropriate sterile injectable medium. Carriers are intended to include necessary and inert binders, suspending agents, lubricants, flavorants, sweeteners, preservatives, dyes, and coatings. The compositions may be further comprised of stabilizers, which as used herein, is a substance which increases the half-life of the morphatide in the blood stream. Polyethylene glycol may be used as a stabilizer. A stabilizer would comprise the composition, for example when the morphatide of the composition is to be degraded after administration so as to deliver a bound therapeutic agent which is to be time released.

The morphatides can be administered orally in the form of a sterile solution or suspension containing other solutes or suspending agents, for example, enough saline or glucose to make the solution isotonic, bile salts, acacia, gelatin, sorbitan monoleate, polysorbate 80 (oleate esters of sorbitol and its anhydrides copolymerized with ethylene oxide) and the like.

The morphatides can also be administered orally either in liquid or solid composition form. Compositions suitable for oral administration include solid forms, such as pills, capsules, granules, tablets, and powders, and liquid forms, such as solutions, syrups, elixirs, and suspensions. Forms useful for parenteral administration include sterile solutions, emulsions, and suspensions.

Optimal dosages to be administered may be determined by those skilled in the art, and will vary with the particular morphatide in use, the strength of the preparation, the mode of administration, and the advancement of the disease condition or abnormality. Additional factors depending on the particular subject being treated will result in a need to adjust dosages, including subject age, weight, gender, diet, and time of administration.

The present invention provides a morphatide labelled with a detectable marker. In an embodiment the detectable marker that is selected from the group consisting of a radioactive isotope, enzyme, dye, biotin, a fluorescent label, a chemiluminescent label and a ligand.

In an embodiment of the above-described compositions wherein the morphatide is incapable of being degraded the composition further comprises a stabilizer molecule for increasing the half-life of the morphatide in the blood stream. In an embodiment the stabilizer is polyethyleneglycol.

This invention provides a method of treating a subject with any of the above-described compositions of morphatides and morphatides conjugated to therapeutic agents.

In another aspect, this invention provides a method of drug delivery to a target in the body of a subject comprising administration to a subject any of the above-described compositions of morphatides and morphatides conjugated to therapeutic agents, thereby delivering the drug to the target.

In an embodiment of the above-described compositions wherein a morphatide is capable of being degraded, the degradation is performed by either of a nuclease or protease.

This invention further provides a method of drug delivery to a target in the body of a subject comprising administration to a subject of the above-described compositions of morphatides and morphatides conjugated to therapeutic agents, wherein the morphatide is incapable of being degraded or is slowly degraded after administration to the subject, thereby delivering the morphatide-bound drug to the target. In an embodiment of the method of drug delivery, wherein the morphatide-bound drug is administered, the administration may be intravenous, intraperitoneal, intrathecal, intralymphatical, intramuscular, intralesional, parenteral, epidural, subcutaneous; by infusion, liposome-mediated delivery, aerosol delivery; topical, oral, nasal, anal, ocular or otic delivery.

In a further embodiment of the above described methods of identifying morphatides, the morphatide is capable of binding to any component of an antibody molecule, said antibody having a constant and variable region.

It will be appreciated to one skilled in the art that the methods of the present invention have several advantages over existing technologies. Among these advantages are the following: agent molecules and scaffolding molecules can be cycled separately or together; a variety of agent molecules and scaffolding molecules can be utilized; in many screening processes, reaction conditions (such as temperature or salt conditions) can be readily modified to enrich, screen, or select for particular association events; linker molecules can be utilized to generate novel secondary and tertiary structures; this is a cell free system, helping to avoid potential background contamination or false results.

In particular, if scaffolding molecules used are nucleic acids, the following advantages are afforded: single stranded, double stranded, triple stranded, or branched nucleic acids can be utilized; analogue nucleic acid molecules can be utilized, further increasing the potential structural diversity of the scaffolding molecule; linker molecules or components of linker molecules can be attached to multiple bases in the nucleic acid molecules; mixtures of bases can be utilized; sequencing can be employed to decipher desirable or resulting scaffolding molecules; mutations can be focused on subdomains within the nucleic acid molecules to modify the scaffolding molecule as desired, if so desired; modified polymerases can be employed for wider utility in the generation of nucleic acid scaffolding molecules, and in the modification process, if this process requires the use of polymerases; and non-degradable nucleic acids can be utilized in this method.

These and other aspects of the present invention will be apparent to those skilled in the art.

This invention will be better understood from the Experimental Details which follow. However, one skilled in the art will readily appreciate that the specific methods and results discussed are merely illustrative of the invention as described more fully in the claims which follow thereafter.

EXPERIMENTAL DETAILS

The following outlines a simple strategy to generate and evolve selected Morphatides.

Example 1
Generation and Amplification of Linker Conjugated Scaffolding Molecules 1) Three pools of nucleic acid scaffolding molecules are generated using sequence randomized template nucleic acids generated (using solid state phosphoamidite chemistry followed by PCR amplification) with phenylboronic acid linker reagent conjugated dUTP molecules and dUTP, dATP, dCTP, and dGTP. Conjugated dUTP molecules are generated utilizing standard chemistry and phenylboronic acid linkers complexing reagents. Different ratios of conjugated dUTP molecules to unconjugated dUTP molecules are present in each pool. Pool #1 contains conjugated:unconjugated dUTP present in a 1:10 ratio; pool #2 contains conjugated:unconjugated dUTP present in a 1:1 ratio; and pool #3 contains conjugated:unconjugated dUTP present in a 10:1 ratio. Error prone PCR is performed on each pool.

Generation of Morphatides

2) Five different conjugated amino acids (leucine, aspartic acid, glutamine, phenylalanine and tyrosine) (generated utilizing standard chemistry and phenylboronic acid complex reagents) are combined to generate a mixture of conjugated agent molecules. Condensation reactions are performed utilizing the resulting mixture and each of the three pools, generating complexes of scaffolding molecules/linker molecules/agent molecules.

Selection and Evolution of Morphatides

3) Selection of thrombin binding Morphatides is performed on each pool as described infra in Example 4.

4) Scaffolding molecules are separated from agent molecules by reversing the linker via a small shift in pH and temperature, and cloned and sequenced as in Example 6.

5) Scaffolding molecules with the same or similar sequences as those obtained in Step 4 are generated via standard solid phase phosphoamidite chemistry, as in step 1, without the use of conjugated nucleotides.

6) Scaffolding molecules of selected Morphatides are then subjected to sexual PCR according to the following protocol to generate modified versions of the selected molecules:
   a) Double stranded DNA from each pool and double stranded DNA from Step 6 are amplified, and free primers are removed from the samples;
   b) About 5 μg of the DNA from each sample is digested with 0.15 units of DNAse I (Sigma, St. Louis, Mo.) in 100 μl of [50 mM Tris-HCl ph 7.4, 1 mM $MgCl_2$], for 10–20 minutes at room temperature. The digested DNA is run on a 2% low melting point agarose gel. Fragments of the desired size range are purified from the 2% low melting point agarose gel by electrophoresis onto DE81 ion exchange paper (Whatman, Hillsborougy, Oreg.). The DNA fragments are then eluted from the paper with 1M NaCl and ethanol precipitated.
   c) Purified fragments are resuspended at a concentration of 10–30 ng/μl in PCR Mix (0.2 mM each dNTP, 22 mM $MgCl_2$, 50 mM KCl, 10 mM Tris-HCl ph 9.0, 0.1% Triton X-100, 0.3 μl Taq DNA polymerase, 50 μl total volume). A reassembly program of 94° C. for 60 seconds, 30–45 cycles of [94° C. for 30 seconds, 50–55° C. for 30 seconds, 72° C. for 30 seconds] and 5 minutes at 72° C. is used in a thermocycler. Reaction can be followed by taking samples after 25, 30, 35, 40 and 45 cycles of reassembly.

Morphatide complexes are regenerated by complexing to agent molecules and new Morphatides are rescreened for binding to thrombin. Process is performed as many times as needed to narrow pool to most desirable Morphatides.

Example 2

Generation and Amplification of Scaffolding Molecules

Generation of Scaffolding Molecules

Four libraries of scaffolding molecules containing a random region (variable cores) and constant flanking regions are constructed. In each case, three of the four bases are incorporated with similar frequencies and one base is represented in a much reduced amount (e.g., $1/10^{th}$ of the other three bases, although this ratio depends upon several factors, including the length of the variable core), hereinafter the "restricted" or "rare" base. The "restricted" base later provides the template for the incorporation of the linker "base" or nucleotide associated with linker molecules (a linker base can be a base analog as well). This approach permits the random modification of the variable cores in a manner that permits the position of the linker bases to be determined. This strategy is termed the 4×(3+1).

In a 4×(3+1) strategy, four pools of ssDNA oligomers with 72 nucleotides are prepared using solid state phosphoamidite chemistry. Eighteen pool specific base positions at the 5' and 3' end are kept constant for primer recognition during PCR. The central 36 positions are randomized by incorporating 3 bases at 31.3% each and one base, containing the linker, at 5%. After deprotection from the solid support, the pools are purified and recovered by precipitation using standard oligonucleotide purification protocols.

Therefore, scaffolding molecule sequences consist of three regions: 1) a fixed 5' sequence of 18 nucleotides, 2) a randomized middle part of 36 nucleotides, and 3) a fixed 3' sequence of 18 nucleotides. The two fixed sequences serve as PCR primer anchor sites. The variable core is synthesized as randomized sequences in four groups or pools. Variable cores in the first pool are synthesized with adenine reduced to 5% of the other bases, in the second pool with similarly reduced G, in the third pool with reduced % C, and in the fourth pool with reduced % T. These are termed the "3+1" reactions indicating that three of the bases are represented in equal amounts while each of the other nucleotides are present at the reduced level. In this manner, four pools of oligonucleotides are created. The rare base is the one that contains the linker molecule that can be connected or associated to agent molecules after each round of amplification-selection. It is the infrequent appearance of this base that reveals the potential sites of association or connection.

The two primer sequence anchors are designed as to not contain the nucleotide that is present in low concentrations in the variable core region. As a consequence, each pool will be anchored by pool specific primer pairs. Linker bases will thus only occur in the random core. This allows the determination of the positions of linker bases by DNA sequencing.

Amplification of Random Pools by PCR

The four pools are subjected individually to PCR amplification using two primers homologous to the anchored sequences. A selection protocol for single stranded DNA (ssDNA) is used. (Bock et al. 1992). These protocols are known in the art. One primer (the reverse primer, corresponding to the complement of the 3' end of the oligomer pools) is biotinylated to allow for later isolation of a single strand. For the rare base [that is present at low levels] in each of the four pools, a nucleotide is used that has the linker group attached. Hence, the rare nucleotides in the 36 nucleotide variable cores in the four pools of oligonucleotides have linker moieties associated or connected to them. The scaffolding molecules are then applied to a streptavidin-agarose column (equilibrated to 0.1 M Tris-HCl, pH 7.5, 0.1 M NaCl) (Griffin et al., 1993; Bock et al., 1992), and ssDNA (corresponding to original sequence library) eluted with 0.15 N NaOH. The flow through fraction (un-biotinylated strand) is collected, neutralized with acetic acid, concentrated and precipitated with ethanol.

Example 3

Generation of Morphatides

The rare DNA bases in the four random pools containing linkers are now individually reacted with the agent molecule threonine via a coupling reaction to generate the morphatides.

Selection of agent molecules to be used can depend on several factors. For example, aliphatic pentynyl groups can provide a site for hydrophobic interaction with a hydrophobic cluster of surface residues on thrombin. Knowledge of essential structures on the target molecule, such as catalytic site may be helpful in considering agent molecules. Of general use are charged groups such as several amino acids (Asp, Glu, and Arg) and hydrophobic moieties such as hydrophobic amino acids (Trp, Tyr, and Phe). However, many similar chemical groups are worthwhile considering. Small peptides are possible too.

Example 4

Selection of Morphatides with Affinity to Thrombin

After PCR amplification the four pools of morphatides are combined. Selection cycles are performed on concanavalin A column immobilized human thrombin (Bock et al. 1992). The DNA from Example 2 is precipitated and dissolved in selection buffer: (20 mM tris-acetate, pH 7.4, 140 mM NaCl, 5 mM KCl, 1 mM $CaCl_2$). The DNA is first applied to a concanavalin A-agarose column to remove those molecules that recognize concanavalin A or agarose structures. The flow through is then applied to a column containing thrombin bound to the concanavalin A-agarose support. The column is washed several times with selection buffer and the binding morphatides (selected morphatides) are eluted with 0.1 M α-methylmannoside, in the selection buffer (Griffin et al., 1993; Bock et al., 1992).

Example 5

Evolution of Selected Morphatides

Selected morphatides are subjected to phenol extraction to remove the thrombin. Scaffolding components are separated from the threonine molecules. The resulting scaffolding molecules are precipitated with 20 μg glycogen and three volumes of ethanol. After resuspending the DNA, the oligomer solution is split into four pools, and amplified under error prone conditions. High fidelity amplification is utilized for the final amplification step, i.e. first sloppy PCR and then high fidelity PCR. For each pool the corresponding "restricted" nucleotide and the appropriate PCR primer sets are used. After PCR amplification the fragments are again reacted with the agent molecules. (Griffin; Bock) A total of six selection cycles over conA-agarose are performed. On average five cycles perform well.

Example 6

Cloning and Sequencing of the Scaffolding Components of High Affinity Morphatides Characterization of the scaffolding components of the high affinity thrombin binding Morphatides after the final selection step is performed by cloning and sequencing of the nucleic acids. Single-stranded DNA (of the scaffolding components) is converted to dsDNA by PCR and cloned into an M13 mp18 based TA modified cloning vector commercially available (Invitrogen Corp.). This vector also serves as a convenient repository for the generation of oligomers by PCR and generation of template for automated rapid DNA sequencing using robust M13 technology. This cloning and sequencing provides the DNA sequences of the selected scaffolding molecules, and, as only the rare nucleotide in each pool has the linker attached, also reveals the information about the position of the agent molecule. The sequencing results from the four random pools are analyzed using DNA alignment and phylogenetic software (widely available and utilized) to establish consensus sequences of the dominant binders.

Example 7

Characterization of Thrombin Specific Morphatides

Determination of Binding Characteristics

Binding constants to thrombin are determined. Because a considerable number of binding and competition experiments are performed, a rapid assay is employed. Thrombin is immobilized on microtiter plates (Tsiang et al. 1995b) and radioactively labeled Morphatides are added in series of different concentrations. After washing steps, the determination of binding constants is performed using rapid computerized phosphoimager technology. Washing steps are well known to one of ordinary skill in the art. Microtiter plates can be prepared in series and stored at 4° C. for several weeks and the experiments performed using 96-well automated pipetting and washing steps. Crucial experiments to investigate cooperative binding effects, competitive binding and number of binding sites will be performed by equilibrium dialysis methods.

Example 8

Preparation of A Synthetic Oligonucleotide Reactive Phenylboronic acid Complexing Reagent of General Formula XIX and Application Thereof (WO 95/20591, "Phenylboronic Acid Complexes" Aug. 3, 1995)

In the initial step of the synthesis 2-[2-(2-chloroethoxy] ethanol is condensed with N-hydroxy-phthalimide by refluxing in dimethylformamide containing one equivalent of triethylamine for 2 days. The product is precipitated by pouring into water, collected by filtration, washed with water, dried in a vacuum dessicator, and used without further purification.

In the second step of the synthesis, the crude product obtained above is refluxed briefly in a mixture of acetic acid and concentrated hydrochloric acid. After cooling, the precipitated phthalic acid is filtered from solution and the filtrate concentrated and then coevaporated repeatedly from small volumes of water to remove traces of acids. Finally, the aminooxy hydrochloride product is neutralized with $NaHCO_3$, extracted in ethyl acetate, dried over anhydrous $MgSO_4$, and concentrated in vacuo.

Synthetic oligonucleotides may be conjugated with a 2-cyanoethyl-N,N-diisopropylphosphoramidite phenylboronic acid complexing reagents, during the final step of an automated solid-phase oligonucleotide synthesis, to afford synthetic oligonucleotides having 5'-pendant phenylboronic acid complexing moieties.

REFERENCES

Allen, P., Worland, S., and Gold, L. (1995). Isolation of high-affinity RNA ligands to HIV-1 integrase from a random pool. Virology 209, 327–336.

Barbas, C., et. al., (September 1991) Proc. Natl. Acad. Sci. USA, 88:7978–7982.

Bartel, D. P., Zapp, M. L., Green, M. R., and Szostak, J. W. (1991). HIV-1 Rev regulation involves recognition of non-Watson-Crick base pairs in viral RNA. Cell 67, 529–536.

Beaudry, A. A. and Joyce, G. F. (1992) "Directed Evolution of an RNA Enzyme" Science 257 (5070)31: 635–641.

Binkley, J., Allen, P., Brown, D. M., Green, L. S., Tuerk, G., and Gold, L. (1995). RNA ligands to human nerve growth factor. Nucl. Acids. Res. 23, 3198–3205.

Biotechniques, (1995) 18(2), 194–196.

Bock, L. C., Griffin, L. C., Latham, J. A., Vermaas, E. H., and Toole, J. J. (1992). Selection of single-stranded DNA molecules that bind and inhibit human thrombin. Nature 355, 564–566.

Bracht, F. and Schroer, K. (1994). Isolation and identification of aptamers from defibrotide that act as thrombin antagonists in vitro. Biochem. Biophys. Res. Comm. 200, 933–937.

Brown, D. and Gold, L. (1995a). Template recognition by an RNA-dependent RNA polymerase: identification and characterization of two RNA binding sites on Q beta replicase. Biochemistry 34, 14765–14774.

Brown, D. and Gold, L. (1995b). Selection and characterization of RNAs replicated by Q beta replicase. Biochemistry 34, 14775–14782.

Burgstaller, P., Kochoyan, M., and Famulok, M. (1995). Structural probing and damage selection of citrulline- and arginine-specific RNA aptamers identify base positions required for binding. Nucl. Acids. Res. 23, 4769–4776.

Castagnoli, L., et. al., (1991) J. Mol. Biol., 222: 301–310.

Chang, C., et. al., (November 1991) The Journal of Immunology, Vol.147, No.10:3610–3614.

Chen, H., McBroom, D. G., Zhu, Y. Q., Gold, L., and North, T. W. (1996). Inhibitory RNA ligand to reverse transcriptase from feline immunodeficiency virus. Biochemistry 35, 6923–6930.

Chen, H. and Gold, L. (1994). Selection of high-affinity RNA ligands to reverse transcriptase: inhibition of cDNA synthesis and RNase H activity. Biochemistry 33, 8746–8756.

Cui, Y., Wang, Q., Stormo, G. D., and Calvo, J. M. (1995). A consensus sequence for binding of Lrp to DNA. J. Bacteriol. 177, 4872–4880.

Clackson, T., et. al., (August 1991) Nature, 352:624–628.

Dobbelstein, M. and Shenk, T. (1995). In vitro selection of RNA ligands for the ribosomal L22 protein associated with Epstein-Barr virus-expressed RNA by using randomized and cDNA-derived RNA libraries. J. Virol. 69, 8027–8034.

Ecker, D. J. et al. (1993) Nucleic Acids Res. 21(8): 1853–1856.

Ellington, A. D. and Szostak, J. W. (1990). In vitro selection of RNA molecules that bind specific ligands. Nature 346, 818–822.

Ellington, A. D. and Szostak, J. W. (1992). Selection in vitro of single-stranded DNA molecules that fold into specific ligand-binding structures. Nature 355, 850–852.

Fan, P., Suri, A. K., Fiala, R., Live, D., and Patel, D. J. (1996). Molecular recognition in the FMN-RNA aptamer complex. J. Mol. Biol. 258, 480–500.

Frantzen, F. (1995) Protein-boronic acid conjugates and their binding to low-molecular-mass cis-diols and glycated hemoglobin. J. Chromatogr. B., Biomed. Appl. 670, 37–45.

Gallop, M. A. et al. (1994) J. of Med. Chem. 37(9) 1233–1251.

Garrard, L., et. al., (December 1991) Biotechnology, 9:1373–1377.

Geiger, A., Burgstaller, P., Von der Eltz, H., Roeder, A., and Famulok, M. (1996). RNA aptamers that bind L-arginine with sub-micromolar dissociation constants and high enantioselectivity. Nucl. Acids. Res. 24, 1029–1036.

Ghisolfi-Nieto, L., Joseph, G., Puvion-Dutilleul, F., Amalric, F., and Bouvet, P. (1996). Nucleolin is a sequence-specific RNA-binding protein: characterization of targets on pre-ribosomal RNA. J. Mol. Biol. 260, 34–53.

Giver, L., Bartel, D. P., Zapp, M. L., Green, M. R., and Ellington, A. D. (1993). Selection and design of high-affinity RNA ligands for HIV-1 Rev. Gene 137, 19–24.

Griffin, L. C., Toole, J. J., and Leung, L. L. K. (1993). The discovery and characterization of a novel nucleotide-based thrombin inhibitor. Gene 137, 25–31.

Hale, S. P. and Schimmel, P. (1996). Protein synthesis editing by a DNA aptamer. Proc. Natl. Acad. Sci. 93, 2755–2758.

Hicke, B. J., Christian, E. L., and Yarus, M. (1989). Stereoselective arginine binding is a phylogenetically conserved property of group I self-splicing RNAs. EMBO J. 8, 3843–3851.

Hoogenboom, H., et. al., (1991) Nucleic Acids Research, Vol.19, No.15:4133–4137.

Houghten, (1985) Proc. Natl. Acad. Sci. USA 82: 5131–5135.

Huizinga, D. E. and Szostak, J. W. (1995). A DNA aptamer that binds adenosine and ATP. Biochemistry 34, 656–665.

Jellinek, D., Green, L. S., Bell, C., and Janjic, N. (1994). Inhibition of receptor binding by high-affinity RNA ligands to vascular endothelial growth factor. Biochemistry 33, 10450–10456.

Jellinek, D., Green, L. S., Bell, C., Lynott, C. K., Gill, N., Vargeese, C., Kirschenheuter, G., McGee, D. P., Abesinghe, P., Pieken, W. A., and et al. (1995). Potent 2'-amino-2'-deoxypyrimidine RNA inhibitors of basic fibroblast growth factor. Biochemistry 34, 11363–11372.

Jellinek, D., Lynott, C. K., Rifkin, D. B., and Janjic, N. (1996). High-affinity RNA ligands to basic fibroblast growth factor inhibit receptor binding. Proc. Natl. Acad. Sci. 90, 11227–11231.

Jenison, R. D., Gill, S. C., Pardi, A., and Polisky, B. (1994). High-resolution molecular discrimination by RNA. Science 263, 1425–1429.

Jensen, K. B., Green, L. S., MacDougal-Waugh, S., and Tuerk, G. (1994). Characterization of an in vitro-selected RNA ligand to the HIV-1 Rev protein. J. Mol. Biol. 235, 237–247.

Jensen, K. B., Atkinson, B. L., Koch, W. M. C., and Gold, L. (1995). Using in vitro selection to direct the covalent attachment of human immunodeficiency virus type I Rev protein to high affinity RNA ligands. Proc. Natl. Acad. Sci. 92, 12220–12224.

Kang, A., et. al., (May 1991) Proc. Natl. Acad. Sci. USA, 88:4363–4366.

Kenan, D. J., Tsai, D. E. and Keene, J. D. (February 1994) TIBS 19, 57–64.

Kluszmann, S., Nolte, A., Bald, R., Erdmann, V. A., and Fuerste, J. P. (1996). Mirror-image RNA that binds D-adenosine. Nature Biotechnology 14, 1112–1115.

Kubik, M. F., Stephens, A. W., Schneider, D., Marlar, R. A., and Tasset, D. (1994). High-affinity RNA ligands to human alpha-thrombin. Nucl. Acids. Res. 22, 2619–2626.

Latham, J. A., Johnson, R., and Toole, J. J. (1994). The application of a modified nucleotide in aptamer selection: novel thrombin aptamers containing 5-(1-pentynyl)-2'-deoxyuridine. Nucl. Acids. Res. 22, 2817–2822.

Lorsch, J. R. and Szostak, J. W. (1994). In vitro selection of RNA aptamers specific for cyanocobalamin. Biochemistry 33, 973–982.

Majerfeld, I. and Yarus, M. (1994). An RNA pocket for an aliphatic hydrophobe. Nature Struct. Biol. 1, 287–292.

Maxam, A. M. and Cilbert, W. (1980) Methods of Enzymol. 65:499–560.

McCafferty, J., et. al., (December 1990) Nature, 348:552–554.

Middle, F. A. (1193). Separation of glycosylated haemoglobins using immobilized phenylboronic acid. Effect of ligand concentration, column operating conditions, and comparison with ion-exchange and isoelectric-focusing. Biochem. J. 209, 771–779.

Morris, K. N., Tarasow, T. M., Julin, C. M., Simons, S. L., Hilvert, D., and Gold, L. (1994). Enrichment for RNA molecules that bind a Diels-Alder transition state analog. Proc. Natl. Acad. Sci. 91, 13028–13032.

Mullinax, R., et. al., (October 1990) Proc. Natl. Acad. Sci. USA,87:8095–8099.

Nieuwlandt, D., Wecker, M., and Gold, L. (1995). In vitro selection of RNA ligands to substance P. Biochemistry 34, 5651–5659.

Nolte, A., Kluszmann, S., Bald, R., Erdmann, V. A., and Fuerste, J. P. (1996). Mirror-design of L-oligonucleotide ligands binding to L-arginine. Nature Biotechnology 14, 1116–1119.

O'Connell, D., Koenig, A., Jennings, S., Hicke, B. J., Han, H. L., Fitzwater, T., Chang, Y. F., Varki, N., Parma, D., and Varki, A. (1996). Calcium-dependent oligonucleotide antagonists specific for L-selectin. Proc. Natl. Acad. Sci. 93, 5883–5887.

Padmanabhan, K., Padmanabhan, K. P., Ferrara, J. D., Sadler, J. E. and A. Tulinsky (1993) The structure of α-thrombin inhibited by a 15-mer single stranded DNA aptamer. J. Biol. Chem. 268, 17651–17654.

Puglisis, J. D., Tan, R., Calnan, B. J., Frankel, A. D., and Williamson, J. R. (1992). Conformation of the TAR RNA-arginine complex by NMR spectroscopy. Science 257, 76–80.

Rawls, R., (Mar. 3, 1997). Mimic Tricks DNA Polymerase, Chem. & Engineering News.

Reynolds, M., Rogrefe, R. I., Jaeger, J. A., Schwartz, D. A., Riley, T. A., Marvin, W. B., Daily, W. J., Vaghefi, M. M., Beck, T. A., Knowles, S. K., Klem, R. E. & Aronld, L. J. Jr (1996). Synthesis and thermodynamics of oligonucleotides containing chirally pure RP methylphosphonate linkages. Nucl. Acids. Res. 24, 4584–4591.

Ringquist, S., Jones, T., Snyder, E. E., Gibson, T., Boni, I., and Gold, L. (1995). High-affinity RNA ligands to *Escherichia coli* ribosomes and ribosomal protein S1: comparison of natural and unnatural binding sites. Biochemistry 34, 3640–3648.

Sassanfar, M. and Szostak, J. W. (1993). An RNA motif that Xf, binds ATP. Nature 364, 550–553.

Schneider, D., Tuerk, G., and Gold, L. (1992). Selection of high affinity RNA ligands to the bacteriophage R17 coat protein. J. Mol. Biol. 228, 862–869.

Schneider, D., Gold, L., and Platt, T. (1993). Selective enrichment of RNA species for tight binding to *Escherichia coli* rho factor. FASEB J. 7, 201–207.

Schneider, D. J., Feigon, J., Hostornsky, Z., and Gold, L. (1995). High-affinity ssDNA inhibitors of the reverse transcriptase of type I human immunodeficiency virus. Biochemistry 34, 9599–9610.

Schultze, P., Macaya, R. F. and J. Feigon (1994) Three-dimensional solution structure of the thrombin-binding DNA aptamer d(GGTTGGTGTGGTTGG). J. Mol. Biol. 235, 1532–1547.

Stemmer, W. P. C. (October 1994) PNAS 91, 10747–10751.

Stemmer, W. P. C., U.S. Pat. No. 5,605,793 issued Feb. 25, 1997, entitled "Methods for In-Vitro Recombination,".

Tsiang, M., Gibbs, G. S., Griffin, L. C., Dunn, K. E. and L. L. K. Leung (1995a) Selection of a suppressor mutation for thrombin using in vitro genetics. J. Biol. Chem. 270, 19370–19376.

Tsiang, M., Jain, A. K., Dunn, K. E., Rojas, M. E., Leung, L. L. K. and G. S. Gibbs (1995b) Functional mapping of the surface residues of human thrombin. J. Biol. Chem. 270: 16854–16863

Tuerk, G., MacDougal, S., and Gold, L. (1992). RNA pseudoknots that inhibit human immunodeficiency virus type I reverse transcriptase. Proc. Natl. Acad. Sci. 89, 6988–6992.

Tuerk, G. and Gold, L. (1990). Systematic evolution of ligands by exponential enrichment: RNA ligands to bacteriophage T4 DNA polymerase. Science 249, 505–510.

Tuerk, G. and MacDougal-Waugh, S. (1993). In vitro evolution of functional nucleic acids: high affinity RNA ligands of HIV-1 proteins. Gene 137, 33–39.

Wang, K. Y., Gerena, L., Swaminathan, S., and Bolton, P. H. (1995). Determination of the number and location of the manganese binding sites of DNA quadruplexes in solution by EPR and NMR. Nucleic Acids Research 23, 844–848.

Wiegand, T. W., Williams, P. B., Dreskin, S. C., Jouvin, M. H., Kinet, J. P., and Tasset, D. (1996). High-affinity oligonucleotide ligands to human IgE inhibit binding to Fc epsilon receptor I. J. Immunol. 157, 221–230.

Yarus, M. and Majerfeld, I. (1992). Co-optimization of ribozyme substrate stacking and L-arginine binding. J. Mol. Biol. 225, 945–949.

Ye, J., Esmon, C. T., and Johnson, A. E. (1993). The chondroitin sulfate moiety of thrombomodulin binds a second molecule of thrombin. J. Biol. Chem. 268, 2373–2379.

Yurkevich, A. M. (1969). The reaction of phenylboronic acid with nucleosides and mononucleotides. Tetrahedron 25, 477–484.

U.S. Pat. No. 5,270,163 for Nucleic Acid Ligands.

PCT/US91/04078 entitled "Nucleic Acid Ligands".

PCT/US94/10562 filed Sep. 19, 1994.

International Patent Application WO 96/09316, entitled "Parallel Selex", Mar. 28, 1996.

International patent application WO 95/20591, entitled "phenylboronic acid complexes", Aug. 3, 1995.

What is claimed is:

1. A nucleic acid scaffold complex comprising:
   (a) a scaffolding component consisting of a nucleic acid subunit comprising nucleotide bases or nucleotide base analogs;
   (b) one or more reversibly associated phenylboronic acid linker components bound to the scaffolding component; and
   (c) one or more threonine residues linked to said nucleic acid subunit by the phenylboronic acid linker components;
   wherein said scaffolding component does not encode said one or more threonine residues, and
   wherein both the scaffolding component and the one or more threonine residues affect binding of said scaffold complex to thrombin.

2. A nucleic acid scaffold complex comprising:
   (a) a scaffolding component consisting of nucleic acid subunits comprising nucleotide bases or nucleotide base analogs; and
   (b) two more non-nucleic acid agent molecules linked to said nucleic acid subunits via a linker;
   wherein each nucleic acid subunit comprises a variable core region,
   wherein said linker comprises a phenylboronic acid linker component,
   wherein the scaffolding component does not encode said agent molecule,
   wherein the scaffolding component is flanked by primer sequence anchors,
   wherein the two or more agent molecules are linked to the scaffolding component at an identical nucleotide at two or more positions of the variable core region,
   wherein the identical nucleotide occurs less frequently in the variable core region than other nucleotides of the variable core region,
   wherein the identical nucleotide is not present in the primer sequence anchors, and wherein both the scaffolding component and the one or more non-nucleic acid agent molecules affect binding of said scaffold complex to a target molecule.

3. The nucleic acid scaffold complex of claim 1, wherein said linker component is covalently bound to said subunit.

4. The nucleic acid scaffold complex of claim 2, wherein said linker component is covalently bound to said subunit.

5. The nucleic acid scaffold complex of claim 1, wherein said linker component is covalently bound to said threonine residue.

6. The nucleic acid scaffold complex of claim 2, wherein said linker component is covalently bound to said agent molecule.

7. A nucleic acid scaffold complex reversibly associated with an agent molecule via a linker component, the complex comprising:

(a) a scaffolding component consisting of a nucleic acid subunit comprising nucleotide bases or nucleotide base analogs;

(b) two or more reversibly associated non-nucleic acid linker components, wherein the linker comprises phenylboronic acid, a thio linker, a DNA binding protein, or biotin bound to streptavidin; and (c) two or more non-nucleic acid agent molecules linked to said subunit;

wherein said scaffolding component does not encode said agent molecule, wherein both the scaffolding component and the two or more non-nucleic acid agent molecules affect binding of said scaffold complex to a target molecule, wherein the nucleic acid subunit comprises a variable core region flanked by primer sequence anchors, wherein two or more agent molecules are linked to the scaffolding component at an identical nucleotide at two or more positions of the variable core region, wherein the identical nucleotide occurs less frequently in the variable core region than other nucleotides of the variable core region, and wherein the identical nucleotide is not present in the primer sequence anchors.

8. The nucleic acid scaffold complex of claim 7, wherein said linker component is selected from the group consisting of phenyl-boronic acid, a thio linker and a biotin-streptavidin linker.

9. The nucleic acid scaffold complex of claim 7, wherein said linker component is covalently bound to said subunit.

10. The nucleic acid scaffold complex of claim 7, wherein said linker component is covalently bound to said agent molecule.

11. The nucleic acid scaffold complex of claim 1, wherein the scaffolding component comprises a variable core region flanked by primer sequence anchors, wherein two or more agent molecules are linked to the scaffolding component at an identical nucleotide at two or more positions of the variable core region, and wherein the identical nucleotide occurs less frequently in the variable core region than other nucleotides of the variable core region, and wherein the identical nucleotide is not present in the primer sequence anchors.

12. A nucleic acid scaffold complex reversibly associated with an agent molecule via a linker component comprising:

(a) a scaffolding component consisting of a nucleic acid subunit comprising nucleotide bases or nucleotide base analogs and (b) two or more non-nucleic acid threonine molecules linked to said subunits via a linker component comprising phenylboronic acid; and wherein the scaffolding component does not encode the agent molecule, wherein the two or more threonine molecules are linked to the scaffolding component at an identical nucleotide at two or more positions of the scaffolding component, wherein the identical nucleotide occurs less frequently in the scaffolding component than other nucleotides of the scaffolding component, and wherein both the scaffolding component and the two or more non-nucleic acid agent molecules affect binding of said scaffold complex to a thrombin target molecule.

13. The method of claim 12, wherein the scaffolding component comprises a variable core region flanked by primer sequence anchors, wherein the two or more threonine molecules are linked to the scaffolding component at an identical nucleotide at two or more positions of the variable core region, wherein the identical nucleotide occurs less frequently in the variable core region than other nucleotides of the variable core region, and wherein the identical nucleotide is not present in the primer sequence anchors.

14. A library of nucleic acid scaffold complexes, wherein each nucleic acid scaffold of the library comprises:

(a) a scaffolding component consisting of a nucleic acid subunit comprising nucleotide bases or nucleotide base analogs, wherein the nucleic acid subunit comprises a variable core region flanked by primer sequence anchors, and wherein the scaffolding component of each nucleic acid scaffold of the library is generated using PCR mutagenesis, error prone PCR, or sexual PCR of a nucleic acid template during an amplification reaction after removal of an agent molecule from a previously selected nucleic acid subunit of a previously selected nucleic acid scaffold complex after release of the agent;

(b) two or more phenylboronic acid linker components; and (c) two or more threonine molecules linked to said subunits by the phenylboronic acid linker components;

wherein said scaffolding component does not encode said agent molecule, wherein the two or more threonine molecules are linked to the scaffolding component at an identical nucleotide at two or more positions of the variable core region, wherein the identical nucleotide occurs less frequently in the variable core region than other nucleotides of the variable core region, and wherein the identical nucleotide is not present in the primer sequence anchors, wherein the target is thrombin, and wherein both the scaffolding component and the one or more non-nucleic acid agent molecules affect a shape of the nucleic acid scaffold complex, thereby affecting an interaction of the nucleic acid scaffold complex with thrombin.

15. The nucleic acid scaffold complex of claim 1, wherein the phenylboronic acid linker is attached to the threonine residues at a carboxyl group on the threonine residues.

16. The nucleic acid scaffold complex of claim 1, wherein the phenylboronic acid linker is attached to the scaffolding component at a phosphate group of a nucleotide base nucleotide base analog.

17. The nucleic acid scaffold complex of claim 7, wherein the two or more non-nucleic acid agent molecules are two or more threonine residues.

18. The nucleic acid scaffold complex of claim 7, wherein the target is thrombin.

19. The nucleic acid scaffold complex of claim 2, wherein the agent is a peptide, antibody, synthetic polymer, or a carbohydrate.

20. The nucleic acid scaffold complex of claim 2, wherein the agent is a threonine residue.

21. The nucleic acid scaffold complex of claim 7, wherein the agent is a threonine residue.

22. The nucleic acid scaffold complex of claim 7, wherein the nucleotide base analogs consist of 5-azo-cytodine, inosine, 7-deaza-guanine, or methylated cytosine.

23. The nucleic acid scaffold complex of claim 7, wherein the linker components are phenylboronic acid, biotin, streptavidin, or a DNA binding protein.

* * * * *